(12) United States Patent
Harrington et al.

(10) Patent No.: US 9,495,511 B2
(45) Date of Patent: Nov. 15, 2016

(54) REMOTE MONITORING SYSTEMS AND METHODS FOR MEDICAL DEVICES

(75) Inventors: Stacey B. Harrington, Attleboro Falls, MA (US); Joel D. Wiesner, St. Peters, MO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/352,608

(22) Filed: Jan. 18, 2012

(65) Prior Publication Data

US 2012/0226771 A1 Sep. 6, 2012

Related U.S. Application Data

(63) Continuation-in-part of application No. 13/037,886, filed on Mar. 1, 2011, now Pat. No. 8,694,600.

(51) Int. Cl.
G06F 15/16 (2006.01)
G06F 19/00 (2011.01)

(52) U.S. Cl.
CPC ......... *G06F 19/3418* (2013.01); *G06F 19/322* (2013.01)

(58) Field of Classification Search
None
See application file for complete search history.

(56) References Cited

U.S. PATENT DOCUMENTS

| | | |
|---|---|---|
| 5,451,839 A | 9/1995 | Rappaport et al. |
| 5,877,675 A | 3/1999 | Rebstock et al. |
| 5,936,539 A | 8/1999 | Fuchs |
| 6,221,012 B1 | 4/2001 | Maschke et al. |
| 6,377,162 B1 | 4/2002 | Delestienne et al. |
| 6,377,806 B1 | 4/2002 | Tokuyoshi |
| 6,442,433 B1 | 8/2002 | Linberg |
| 6,519,569 B1 | 2/2003 | White et al. |
| 6,578,002 B1 | 6/2003 | Derzay et al. |
| 6,790,198 B1 | 9/2004 | White et al. |
| 6,831,557 B1 | 12/2004 | Hess |
| 6,839,753 B2 | 1/2005 | Biondi et al. |
| 6,907,387 B1 | 6/2005 | Reardon |
| 7,028,182 B1 | 4/2006 | Killcommons |

(Continued)

FOREIGN PATENT DOCUMENTS

| | | |
|---|---|---|
| CA | 2 644 695 | 1/2004 |
| CA | 2 648 885 | 11/2007 |

(Continued)

OTHER PUBLICATIONS

Response filed Feb. 18, 2014 for Office Action dated Sep. 27, 2013 for U.S. Appl. No. 13/241,620; 24 pages.

(Continued)

*Primary Examiner* — Joshua Joo

(57) ABSTRACT

A remote monitoring system for monitoring a plurality of medical devices at a patient care or home care facility. The system includes a device integration server in communication with wireless relay modules for receiving data packets from the medical devices including an identifier and data for each medical device. The system also includes an outbound web server. The web server is configured to provide webpages including the data of the medical devices for display on first and second remote monitoring devices, subject to authentication of an associated data request from the monitoring device.

24 Claims, 11 Drawing Sheets

(56) References Cited

U.S. PATENT DOCUMENTS

| | | |
|---|---|---|
| 7,050,984 B1 | 5/2006 | Kerpelman et al. |
| 7,079,035 B2 | 7/2006 | Bock et al. |
| 7,082,460 B2 | 7/2006 | Hansen et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,411,491 B2 | 8/2008 | Klabunde et al. |
| 7,508,787 B2 | 3/2009 | Doshi et al. |
| 7,512,889 B2 | 3/2009 | Newell et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,605,714 B2 | 10/2009 | Thompson et al. |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,848,819 B2 * | 12/2010 | Goetz et al. ............ 607/59 |
| 7,873,772 B2 | 1/2011 | Waldhoff et al. |
| 7,937,370 B2 | 5/2011 | Hansen |
| 7,942,844 B2 | 5/2011 | Moberg et al. |
| 7,949,404 B2 | 5/2011 | Hill |
| 7,978,062 B2 | 7/2011 | LaLonde |
| 8,002,701 B2 | 8/2011 | John et al. |
| RE42,934 E | 11/2011 | Thompson |
| 8,073,008 B2 | 12/2011 | Mehta et al. |
| 8,095,381 B2 * | 1/2012 | Simons et al. ............ 705/2 |
| 8,108,543 B2 | 1/2012 | Hansen |
| 8,125,318 B2 | 2/2012 | Heimbrock et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,200,195 B2 | 6/2012 | Le Saint et al. |
| 8,214,549 B2 | 7/2012 | Dicks et al. |
| 8,279,061 B2 | 10/2012 | Soliman |
| 8,326,648 B2 | 12/2012 | Kenedy et al. |
| 8,373,556 B2 | 2/2013 | LaLonde et al. |
| 8,395,498 B2 | 3/2013 | Gaskill et al. |
| 8,428,722 B2 | 4/2013 | Verhoef et al. |
| 8,515,547 B2 | 8/2013 | Mass et al. |
| 8,587,427 B2 | 11/2013 | LaLonde et al. |
| 8,694,600 B2 | 4/2014 | Gaines et al. |
| 8,818,260 B2 | 8/2014 | Gaines et al. |
| 8,855,550 B2 | 10/2014 | Gaines et al. |
| 2002/0178126 A1 | 11/2002 | Beck et al. |
| 2002/0178128 A1 | 11/2002 | Beck et al. |
| 2002/0198473 A1 | 12/2002 | Kumar et al. |
| 2004/0024384 A1 * | 2/2004 | Novak ............ 606/1 |
| 2004/0034284 A1 | 2/2004 | Aversano et al. |
| 2004/0155772 A1 | 8/2004 | Medema et al. |
| 2004/0204743 A1 * | 10/2004 | McGrath et al. ............ 607/5 |
| 2005/0055242 A1 | 3/2005 | Bello et al. |
| 2005/0185398 A1 | 8/2005 | Scannell, Jr. |
| 2005/0188853 A1 | 9/2005 | Scannell, Jr. |
| 2005/0201300 A1 | 9/2005 | Bridgelall |
| 2005/0206518 A1 | 9/2005 | Welch et al. |
| 2005/0288571 A1 | 12/2005 | Perkins et al. |
| 2006/0066449 A1 | 3/2006 | Johnson |
| 2006/0074462 A1 | 4/2006 | Verhoef |
| 2006/0074465 A1 * | 4/2006 | Webb ............ 607/60 |
| 2006/0121846 A1 | 6/2006 | Mazar et al. |
| 2006/0154642 A1 | 7/2006 | Scannell, Jr. |
| 2006/0189854 A1 * | 8/2006 | Webb et al. ............ 600/300 |
| 2006/0224048 A1 | 10/2006 | Devaul et al. |
| 2006/0226960 A1 | 10/2006 | Pisz et al. |
| 2006/0238333 A1 | 10/2006 | Welch et al. |
| 2006/0252999 A1 | 11/2006 | Devaul et al. |
| 2007/0100396 A1 | 5/2007 | Freeberg |
| 2007/0135866 A1 | 6/2007 | Baker et al. |
| 2007/0156033 A1 | 7/2007 | Causey, III et al. |
| 2007/0180140 A1 * | 8/2007 | Welch et al. ............ 709/238 |
| 2007/0186923 A1 | 8/2007 | Poutiatine et al. |
| 2007/0216764 A1 | 9/2007 | Kwak |
| 2007/0230197 A1 | 10/2007 | Scannell, Jr. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255250 A1 | 11/2007 | Moberg et al. |
| 2007/0257788 A1 | 11/2007 | Carlson et al. |
| 2007/0258395 A1 | 11/2007 | Jollota et al. |
| 2007/0265533 A1 | 11/2007 | Tran |
| 2007/0268687 A1 | 11/2007 | Scannell, Jr. |
| 2007/0272670 A1 | 11/2007 | Chen |
| 2007/0275270 A1 | 11/2007 | Tran |
| 2007/0276270 A1 | 11/2007 | Tran |
| 2008/0001735 A1 | 1/2008 | Tran |
| 2008/0004904 A1 | 1/2008 | Tran |
| 2008/0004907 A1 | 1/2008 | Bayne |
| 2008/0024294 A1 | 1/2008 | Mazar |
| 2008/0071234 A1 | 3/2008 | Kelch et al. |
| 2008/0075028 A1 | 3/2008 | Park et al. |
| 2008/0088436 A1 | 4/2008 | Reeves et al. |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0103370 A1 | 5/2008 | Dicks et al. |
| 2008/0108880 A1 | 5/2008 | Young et al. |
| 2008/0136652 A1 | 6/2008 | Vaisnys et al. |
| 2008/0139890 A1 | 6/2008 | Craine et al. |
| 2008/0146277 A1 | 6/2008 | Anglin et al. |
| 2008/0146890 A1 | 6/2008 | LeBoeuf et al. |
| 2008/0183502 A1 | 7/2008 | Dicks et al. |
| 2008/0222711 A1 | 9/2008 | Michaelis |
| 2008/0224852 A1 | 9/2008 | Dicks et al. |
| 2008/0228045 A1 | 9/2008 | Gao et al. |
| 2008/0247760 A1 | 10/2008 | Edmon et al. |
| 2008/0281168 A1 | 11/2008 | Gibson et al. |
| 2008/0294019 A1 | 11/2008 | Tran |
| 2008/0294020 A1 | 11/2008 | Sapounas |
| 2009/0019061 A1 | 1/2009 | Scannell, Jr. |
| 2009/0023391 A1 | 1/2009 | Falck |
| 2009/0034441 A1 * | 2/2009 | Budampati ............ H04L 45/00 370/310 |
| 2009/0036750 A1 | 2/2009 | Weinstein et al. |
| 2009/0054948 A1 * | 2/2009 | Webb ............ 607/31 |
| 2009/0058635 A1 | 3/2009 | LaLonde et al. |
| 2009/0058636 A1 | 3/2009 | Gaskill et al. |
| 2009/0062887 A1 | 3/2009 | Mass et al. |
| 2009/0063187 A1 | 3/2009 | Johnson et al. |
| 2009/0063193 A1 | 3/2009 | Barton et al. |
| 2009/0069642 A1 | 3/2009 | Gao et al. |
| 2009/0073694 A1 | 3/2009 | Scannell, Jr. |
| 2009/0105549 A1 | 4/2009 | Smith et al. |
| 2009/0115628 A1 | 5/2009 | Dicks et al. |
| 2009/0128320 A1 | 5/2009 | Needham et al. |
| 2009/0140851 A1 | 6/2009 | Graves et al. |
| 2009/0149722 A1 | 6/2009 | Abolfathi et al. |
| 2009/0184835 A1 | 7/2009 | Deaver, Sr. et al. |

(56) References Cited

U.S. PATENT DOCUMENTS

| | | |
|---|---|---|
| 2009/0203329 A1 | 8/2009 | White et al. |
| 2009/0234672 A1 | 9/2009 | Dicks et al. |
| 2009/0240120 A1 | 9/2009 | Mensinger et al. |
| 2009/0247114 A1 | 10/2009 | Sennett et al. |
| 2009/0252117 A1 | 10/2009 | Sherman et al. |
| 2009/0306747 A1* | 12/2009 | Fischer et al. .................. 607/60 |
| 2009/0326339 A1 | 12/2009 | Horvitz |
| 2010/0011000 A1* | 1/2010 | Chakra et al. .................... 707/9 |
| 2010/0027518 A1 | 2/2010 | Wang |
| 2010/0046417 A1* | 2/2010 | Tamura .................. H04B 7/155 370/315 |
| 2010/0076789 A1 | 3/2010 | Pan |
| 2010/0077115 A1 | 3/2010 | Rofougaran |
| 2010/0080200 A1 | 4/2010 | Stewart |
| 2010/0082371 A1* | 4/2010 | Kamp et al. ...................... 705/3 |
| 2010/0085948 A1 | 4/2010 | Yu et al. |
| 2010/0094098 A1 | 4/2010 | Smith et al. |
| 2010/0117835 A1 | 5/2010 | Nanikashvili |
| 2010/0138235 A1 | 6/2010 | Marks et al. |
| 2010/0166170 A1 | 7/2010 | East et al. |
| 2010/0198142 A1 | 8/2010 | Sloan et al. |
| 2010/0217723 A1 | 8/2010 | Sauerwein, Jr. et al. |
| 2010/0219250 A1 | 9/2010 | Wang |
| 2010/0222645 A1 | 9/2010 | Nadler et al. |
| 2010/0234695 A1 | 9/2010 | Morris |
| 2010/0238854 A1 | 9/2010 | Kazmi et al. |
| 2010/0260061 A1 | 10/2010 | Bojahra et al. |
| 2010/0279647 A1 | 11/2010 | Jacobs et al. |
| 2010/0292556 A1* | 11/2010 | Golden ........................ 600/364 |
| 2010/0315225 A1 | 12/2010 | Teague |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032818 A1 | 2/2011 | Yamaguchi et al. |
| 2011/0032822 A1 | 2/2011 | Soomro |
| 2011/0066555 A1 | 3/2011 | Dicks et al. |
| 2011/0078441 A1 | 3/2011 | Dicks et al. |
| 2011/0087756 A1 | 4/2011 | Biondi et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0148624 A1* | 6/2011 | Eaton et al. ............. 340/539.13 |
| 2011/0158430 A1 | 6/2011 | Dicks et al. |
| 2011/0161111 A1 | 6/2011 | Dicks et al. |
| 2011/0176490 A1 | 7/2011 | Mehta et al. |
| 2011/0179405 A1 | 7/2011 | Dicks et al. |
| 2011/0255454 A1 | 10/2011 | Hauser et al. |
| 2011/0273287 A1 | 11/2011 | LaLonde et al. |
| 2011/0280224 A1 | 11/2011 | Falck et al. |
| 2011/0282671 A1 | 11/2011 | Dicks et al. |
| 2012/0108917 A1* | 5/2012 | Libbus et al. ................ 600/301 |
| 2012/0182143 A1 | 7/2012 | Gaines et al. |
| 2012/0182894 A1 | 7/2012 | Gaines et al. |
| 2012/0182924 A1 | 7/2012 | Gaines et al. |
| 2012/0182927 A1 | 7/2012 | Wiesner et al. |
| 2012/0184207 A1 | 7/2012 | Gaines et al. |
| 2012/0184237 A1 | 7/2012 | Gaines et al. |
| 2012/0185268 A1 | 7/2012 | Wiesner et al. |
| 2012/0226768 A1 | 9/2012 | Gaines et al. |
| 2012/0226771 A1 | 9/2012 | Harrington et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0066644 A1 | 3/2013 | Dicks et al. |
| 2013/0147622 A1 | 6/2013 | LaLonde et al. |
| 2013/0154851 A1 | 6/2013 | Gaskill et al. |
| 2013/0162426 A1 | 6/2013 | Wiesner et al. |
| 2013/0310896 A1 | 11/2013 | Mass |
| 2014/0062718 A1 | 3/2014 | LaLonde et al. |
| 2014/0142979 A1 | 5/2014 | Mitsunaga |
| 2014/0152466 A1 | 6/2014 | Wiesner et al. |

FOREIGN PATENT DOCUMENTS

| | | |
|---|---|---|
| CA | 2 644 635 | 8/2008 |
| CN | 101152077 A | 4/2008 |
| CN | 101902953 | 12/2010 |
| CN | 101938513 | 1/2011 |
| CN | 102265580 A | 11/2011 |
| EP | 0766946 | 4/1997 |
| EP | 2 187 675 A1 | 5/2010 |
| EP | 2 227 063 | 9/2010 |
| JP | 2154131 | 6/1990 |
| JP | 318346 | 1/1991 |
| JP | 11-262492 | 9/1999 |
| JP | 2001268106 A | 9/2001 |
| JP | 2001516097 | 9/2001 |
| JP | 200217691 | 1/2002 |
| JP | 20022251461 | 9/2002 |
| JP | 2003109160 | 4/2003 |
| JP | 2004110486 | 4/2004 |
| JP | 2005-278727 | 10/2005 |
| JP | 2005297618 A | 10/2005 |
| JP | 2005341290 A | 12/2005 |
| JP | 2006-013734 | 1/2006 |
| JP | 2006500205 A | 1/2006 |
| JP | 2006214757 A | 8/2006 |
| JP | 2006520657 | 9/2006 |
| JP | 2006-263181 | 10/2006 |
| JP | 2006-527519 | 11/2006 |
| JP | 2007-208635 | 8/2007 |
| JP | 2007531442 | 11/2007 |
| JP | 2008108170 | 5/2008 |
| JP | 2009-536715 A | 1/2009 |
| JP | 2009-038539 | 2/2009 |
| JP | 2009038539 A | 2/2009 |
| JP | 2009159523 A | 7/2009 |
| JP | 2009199508 A | 9/2009 |
| JP | 2009-246419 | 10/2009 |
| JP | 2009-535929 | 10/2009 |
| JP | 2009-538572 | 11/2009 |
| JP | 101601040 A | 12/2009 |
| JP | 2010516179 A | 5/2010 |
| JP | 2010-524050 | 7/2010 |
| JP | 2011-502369 | 1/2011 |
| JP | 2011-502369 A | 1/2011 |
| JP | 2011500205 A | 1/2011 |
| JP | 2011500206 A | 1/2011 |
| JP | 2011-513019 | 4/2011 |
| JP | 2011513019 A | 4/2011 |
| JP | 2012520144 A | 9/2012 |
| JP | 2012-529926 | 11/2012 |
| JP | 2013-532428 | 8/2013 |
| KR | 10-2008-0016458 | 2/2008 |
| KR | 10-2009-0122968 | 12/2009 |
| KR | 10-2010-0028318 | 3/2010 |
| KR | 20100070064 | 6/2010 |
| WO | WO 94/16617 | 4/1994 |
| WO | WO 98/14228 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2004/084720 A2 | 10/2004 |
| WO | WO 2004/109992 A1 | 12/2004 |
| WO | WO 2005/057294 A1 | 6/2005 |
| WO | WO 2006/057834 A2 | 6/2005 |
| WO | WO 2005/098736 A2 | 10/2005 |
| WO | WO 2007/124091 A1 | 11/2007 |
| WO | WO 2007/127879 A2 | 11/2007 |
| WO | WO 2007/127880 A2 | 11/2007 |
| WO | WO 2007/140025 | 12/2007 |
| WO | WO 2008/052034 A1 | 5/2008 |
| WO | WO 2008/097316 A1 | 8/2008 |
| WO | WO 2009/032134 | 3/2009 |
| WO | WO 2009/032134 A2 | 3/2009 |
| WO | WO 2009/051830 A1 | 4/2009 |
| WO | WO 2009/063303 A1 | 6/2009 |
| WO | WO 2009/129835 A1 | 10/2009 |
| WO | WO 2010/085138 A2 | 7/2010 |
| WO | WO 2010/105063 A1 | 9/2010 |
| WO | WO 2010/144720 A1 | 12/2010 |

(56) References Cited

FOREIGN PATENT DOCUMENTS

| WO | WO 2011/153507 | 12/2011 |
|---|---|---|
| WO | WO 2011153507 A2 | 12/2011 |
| WO | WO 2012097112 A2 | 7/2012 |
| WO | WO 2013/095990 A1 | 6/2013 |
| WO | WO 2013/095991 A1 | 6/2013 |

OTHER PUBLICATIONS

Response filed Feb. 13, 2014 for Office Action dated Sep. 5, 2013 for U.S. Appl. No. 13/006,769, 18 pages.
Request for Continued Examination filed Jan. 24, 2014; for U.S. Appl. No. 13/037,886; 2 pages.
Response filed with RCE on Feb. 13, 2014 for Final Office Action dated Dec. 2, 2013 for U.S. Appl. No. 13/006,784; 24 pages.
European Response filed Mar. 3, 2014; to Official Communication dated Aug. 22, 2013; and to the Written Opinion; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. Appl. No. PCT/US2013/059703; 12 pages.
Office Action dated May 22, 2013; for U.S. Appl. No. 13/037,886; 14 pages.
Notice of Allowance; dated Oct. 9, 2013; for U.S. Appl. No. 13/037,886; 11 pages.
Response filed Aug. 14, 2013; to Office Action dated May 15, 2013; for U.S. Appl. No. 13/006,784; 13 pages.
European Comments on Written Opinion dated Nov. 8, 2013; for EP Pat. App. No. 12708203.0; 2 pages.
Final Office Action dated Dec. 2, 2013; for U.S. Appl. No. 13/006,784; 38 pages.
Atmel Corporation, "ZigBee PRO Stack and Software Development Kit," http://www.meshnetics.com/wsn-software/, Nov. 4, 2011.
Bacheldor, "Hospital Tries ZigBee to Track Patients," RFID Journal, Jul. 21, 2006.
BelAir Networks, "Capacity of Wireless Mesh Networks," white paper, 2006.
Bogia, "Enabling the future of u-Health-IEEE 11073 Personal Health Device Standards," slides, Sep. 16, 2009.
Bowman, "Newly Ratified ZigBee Health Care Profile Now Available for Public Download," http://www.fiercehealthcare.com/node/40708, Apr. 6, 2010.
Craig, "ZigBee Networks," http://medicaldesign.com/electrical-components/zigbee_networks/, Apr. 1, 2005.
Craig, "ZigBee: 'Wireless Control That Simply Works'," https://docs.zigbee.org/zigbee-docs/dcn/04-1427.pdf, prior to Jan. 2011.
Digi International Inc., "ConnectPort® X4 H," retrieved from the Internet: http://www.digi.com, 2008-2010.
Digi International Inc., "Demystifying 802.15.4 and ZigBee®," white paper, retrieved from the Internet: http://www.digi.com, 2008-2010.
Digi International Inc., "XBee® & XBee-PRO® ZB," retrieved from the Internet: http://www.digi.com, 2008-2010.
Digi International Inc., "XBee® & XBee-PRO® ZB ZigBee® PRO RF Modules," http://www.digi.com/products/wireless/zigbee-mesh/xbee-zb-module.jsp, Nov. 2, 2010.
Dvorak, "Remote Monitoring," http://medicaldesign.com/electrical-components/remote_monitoring/index.html, Apr. 1, 2005.
ENP Newswire, "Freescale products achieve ZigBee Health Care Certification," May 19, 2010.
Huang, "Medical electronics: from hospital and clinic to the home," http://www.eetimes.com/General/DisplayPrintViewContent?contentItemid=4211247, Dec. 8, 2010.
ICP DAS, "ZigBee Converter User's Manual," Sep. 22, 2008.
Le, "Designing a ZigBee-ready IEEE 802.15.4-compliant radio transceiver," http://rfdesign.com/mag/411rfdf4.pdf, Nov. 2004.
Norris et al., "Single-chip ZigBee for Indoor Mobile Telemetry," presentation, Jun. 21, 2005.
Pinto, "WMM—Wireless Mesh Monitoring," Technical report, 2009.
Sailhan et al., "Wireless Mesh Network Monitoring: Design, Implementation and Experiments, " In proc. of IEEE Workshop on Distributed Autonomous Network Management (DANMS), 2007.
Skibniewski et al, "Ubiquitous Computing: Object Tracking and Monitoring Inconstruction Processes Utilizing Zigbee™ Networks," The 23th International Symposium on Automation and Robotics in Construction (ISARC2006), Oct. 3-5, Tokyo, Japan.
Stewart, "Build reliable Zigbee-based solutions," EE Times-Asia, Apr. 16-30, 2007.
Texas Instruments, "Choose your ZigBee solution with TI," 1Q 2010.
Texas Instruments, "Consumer Medical Applications Guide," retrieved from the Internet: http://www.ti.com/medical, 2010.
Texas Instruments, "RF/IF and ZigBee® Solutions," http://focus.ti.com/analog/docs/gencontent.tsp? familyid=367&genContentid=24190&DC . . . , Dec. 8, 2010.
Texas Instruments, "ZigBee® Wireless Networking Overview," 1 page, 2010.
The Silicon Horizon Inc., "techFX Zigbee rev A-techFX Zigbee Tools v 1.0," 2007-2008.
Tutorial-Reports.com, "Zigbee Tutorial," http://www.tutorial-reports.com/book/print/152, Nov. 1, 2010.
Unknown author, "The Nokia Network Monitor Introduction," http://www.panuworld.net/nuukiaworld/misc/netmon/index.htm, Oct. 30, 2005.
Verse!, "ZigBee Alliance ratifies wireless protocol for low-power medical devices," retrieved from the Internet: http://www.fiercemobilehealthcare.com, Apr. 6, 2010.
Wellspring, "Router, Gateway, Base Station, Cell Modem Specification and Submittal," http://www.h2odegree.com/documents/ReferenceLibrary/OtherProductLiterature/RouterGatewayBaseSpecSheetSubmittal.pdf, 5 pages, prior to Jan. 2011.
Wellspring, "Wellspring Switches to a ZigBee-Cellular Hybrid System," press release, Feb. 20, 2006.
ZigBee Alliance, "ZigBee Wireless Sensor Applications for Health, Wellness and Fitness," https://docs.zigbee.org/zigbee-docs/dcn/09-4962.pdf, Mar. 2009.
PCT Search Report and Written Opinion of the ISA; dated Apr. 1, 2013; for PCT Pat. App. No. PCT/US2012/0638892; 12 pages.
PCT Search Report and Written Opinion of the ISA; dated Apr. 1, 2013; for PCT Pat. App. No. PCT/US2012/068888; 15 pages.
PCT Search Report and Written Opinion; dated Apr. 1, 2013; for PCT Pat. App. No. PCT/US2012/068888; 15 pages.
Response to Office Action; dated Nov. 15, 2012; for U.S. Appl. No. 13/037,886; 14 pages.
Amendment filed Mar. 26, 2014, to Office Action dated Dec. 27, 2013; for U.S. Appl. No. 13/352,575; 12 pages.
Amendment filed Mar. 26, 2014; to Office Action dated Jan. 7, 2014; for U.S. Appl. No. 13/353,565; 15 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.
PCT Search Report and Written Opinion of the ISA; dated Apr. 29, 2013; for PCT Pat. App. No. PCT/US2013/021530; 10 pages.
Office Action dated Sep. 5, 2013, for U.S. Appl. No. 13/006,769, 36 pages.
Response filed Feb. 13, 2014 for Office Action dated Sep. 5, 2013 for U.S. Appl. No. 13/006,769; 18 pages.
Office Action dated Jan. 7, 2014; U.S. Appl. No. 13/353,565; 33 pages.
Office Action dated Dec. 27, 2013; for U.S. Appl. No. 13/352,575; 31 pages.
Notice of Allowance dated Apr. 30, 2014; for U.S. Appl. No. 13/241,620; 21 pages.
Mexican Official Action received May 2, 2014, for Mexican Pat. App. No. MX/A2013/008157; 3 pages.

(56) References Cited

OTHER PUBLICATIONS

PCT International Preliminary Report on Patentability of the ISA; dated Sep. 12, 2013; for PCT Pat. App. No. PCT/US2012/025906; 14 pages.
Mexican Notice of Allowance dated May 7, 2014; for Mexican Pat. App. No. MX/a/2013/009985; 2 pages.
Mexican Office Action received Apr. 22, 2014; for Mexican Pat. App. No. MX/a/2013/008154; 4 pages.
Response to Office Action dated Apr. 29, 2014 for U.S. Appl. No. 13/352,608, filed Jan. 18, 2012.
Notice of Allowance dated Jun. 6, 2014 for U.S. Appl. No. 14/154,285, filed Jan. 14, 2014.
Notice of Allowance dated Jun. 9, 2014 for U.S. Appl. No. 13/006,769, filed Jan. 14, 2011.
Office Action dated Jun. 16, 2014 for U.S. Appl. No. 13/353,565, filed Jan. 19, 2012.
Japanese Office Action dated May 30, 2014 for Application No. 2013-549531.
Notice of Allowance for U.S. Appl. No. 13/352,575, filed Jan. 18, 2012.
Office Action dated Jun. 20, 2014 for U.S. Appl. No. 13/334,447, filed Dec. 22, 2011.
European Search Report dated Jun. 14, 2014; for European Patent Application No. 14168075.1-1951; 8 pages.
Office Acton dated Jun. 23, 2014 for U.S. Appl. No. 13/334,459, filed Dec. 22, 2011 44 pages.
U.S. Response to 312 Amendment dated Jul. 21, 2014; for U.S. Appl. No. 14/154,285; 3 pages.
Japanese Office Action (including English translation) dated Jun. 23, 2014; for Japanese Pat. App. No. 2013-549532 6 pages.
PCT International Preliminary Report on Patentability of the ISA dated Jul. 3, 3014; for PCT Pat. App. No. PCT/U52012/068892; 8 pages.
PCT International Preliminary Report on Patentabiiity of the ISA dated Jul. 3, 2014; for PCT Pat. App. No. PCT/US2012/068888; 8 pages.
Singapore Written Opinion dated Jun. 18, 2014; for Singapore Pat. App. No. 2013053236; 11 pages.
Singapore Written Opinion dated Jun. 19, 2014; for Singapore Pat. App. No. 2013065230; 22 pages.
Response filed (with English Language Passage) of Mexican Office Action received Jul. 7, 2014; for Mexican Pat. App. No. MX/a/2013/008154; 16 pages.
Miche et al.; "The Internet of Vehicles of the Second Generation of Telematic Services;" ERCIM, Paris, FR; vol. 77; Apr. 2, 2009; pp. 43-45.
PCT Search Report and Written Opinion of the ISA; for PCT Pat. App. No. PCT/US2012/021007; dated Sep. 20, 2012; 16 pages.
PCT Search Report and Witten Opinion of the ISA for PCT Pat. App. No. PCT/US2012/068895; dated Mar. 15, 2013; 14 pages.
PCT Search Report and Written Opinion of the ISA; for PCT Pat. App. No. PCT/US2013/020069; dated Feb. 1, 2013; 16 pages.
PCT Search Report and Written Opinion of the ISA; for PCT Pat. App. No. PCT/US2013/020071; dated Feb. 1, 2013; 10 pages.
Response filed Jul. 12, 2013; to Final Office Action dated May 22, 2013; for U.S. Appl. No. 13/037,886; 14 pages.
Office Action; dated May 15, 2013; for U.S. Appl. No. 13/006,784; 35 pages.
Article 19 Amendment; dated Nov. 16, 2012; for PCT Pat. App. No. PCT/US2012/021007; 7 pages.
Article 19 Amendment; dated Feb. 4, 2013; for PCT Pat. App. No. PCT/US2012/025906; 9 pages.
PCT International Preliminary Report on Patentability; dated Jul. 25, 2013; for PCT Pat. App. No. PCT/US2012/021007; 12 pages.
PCT International Search Report; dated Aug. 2, 2012; for PCT Pat. App. No. PCT/US2012/021008.
PCT International Preliminary Report on Patentability; dated Jul. 25, 2013; for PCT Pat. App. No. PCT/US2012/021008; 7 pages.
Kawai et al.; "Proposal of an Assured Corridor Mechanism for Urgent Information Transmission in Wireless Sensor Networks;" IEICE Transactions on Communications, Communications Society, Tokyo, Japan; vol. E90B, No. 10; Oct. 1, 2007; pp. 2817-2826.
PCT Search Report and Written Opinion of the ISA; dated Dec. 3, 2012; for PCT Pat. App. No. PCT/2012/025906; 19 pages.
Office Action dated Nov. 16, 2012; for U.S. Appl. No. 13/037,886; 19 pages.
Notice of Allowance dated Aug. 20, 2014, for U.S. Appl. No. 13/334,447; 25 pages.
Notice of Allowance dated Aug. 15, 2014; for U.S. Appl. No. 13/334,459; 20 pages.
PCT International Preliminary Report on Patentablilty and Written Opinion of the ISA dated Jul. 31, 2014; for PCT Pat. App. No. PCT/US2013/021530; 8 pages.
U.S. Appl. No. 14/462,025, filed Aug. 18, 2014, Wiesner et al.
Gaines et al. "Improved Wireless Relay Module for Remote Monitoring Systems;" U.S. Appl. No. 14/308,881, filed Jun. 19, 2014; 36 pages.
Office Action dated Sep. 9, 2014; for U.S. Appl. No. 13/353,565; 24 pages.
Canadian Office Action dated Aug. 4, 2014; for Canadian Pat. App. No. 2,823,600; 3 pages.
Notice of Allowance dated Sep. 22, 2014; for U.S. Appl. No. 13/006,784; 47 pages.
Mexican Memo concerning the Official Action dated Sep. 19, 2014; regarding Mexican Office Action for Mexican Patent Application No. MX/A/2013/008157; 1 page.
Japanese Amendment and Argument with Claims and Argument in English dated Sep. 22, 2014; for Japanese Pat. App. No. 2013-549532; 28 pages.
PCT International Preliminary Report on Patentability and Written Opinion of the ISA dated Apr. 29, 2014; for PCT Pat. App. No. PCT/US2013/021530; 10 pages.
Australian Patent Examination Report No. 1 dated Sep. 1, 2014; for Australian Pat. App. No. 2012205515; 3 pages.
European Search Report Sep. 18, 2014; for European Pat. Ap. No. 14167899.5; 9 pages.
Canadian Office Action dated Aug. 8, 2014; for Canadian Pat. App. No. 2,823,700; 7 pages.
Australian Examiner's Report dated Sep. 1, 2014; for Australian Pat. App. No. 2012205515; 3 pages.
Korean Notice of Preliminary Rejection, including English translation, dated Oct. 21, 2014; for Korean Pat. App. No. 10-2013-7018317; 7 pages.
Response filed Oct. 27, 2014; to Office Action dated Sep. 9, 2014; of U.S. Pat. App. No. 13/353,565; 20 pages.
Singapore Request for Combined Search and Examination Report, including English Specification, filed Aug. 29, 2014; for Singapore Pat. App. No. 11201403422P; 8 pages.
Russian Office Action dated Oct. 16, 2014; for Russian Pat. App. No. 2013121827/08'4 pages.
Microvision, Inc. Product literature for Microvision Wearable Displays, available at www.microvision.com, copyright 1996-2009, 5 pages.
Eurotech Group, Zypad WR11xx—Rugged Wearable Computer, Product Announcement, available at http://www.zypad.com/zypad/news.aspx?pg=news&id=99, Nov. 17, 2008, 1 page.
Eurotech Group, Zypad WL1100 data sheet, available at http://www.eurotech.com/downloadarea/Datasheets/Wearable%20Computers/Zypad%20WL%201100_sf.pdf, possibly dated Sep. 9, 2008, 2 pages.
Corventis, Inc., Product literature—Wireless cardiovascular solutions for continuous patient surveillance, available at http://corventis.com/US/medprof.asp, copyright 2009, 1 page.
Corventis, Inc., Product literature for NUVANT Mobile Cardiac Telemetry (MCT) System, available at http://corventis.com/US/nuvant.asp, copyright 2009, 2 pages.
Corventis, Inc., Product literature for AVIVO Mobile Patient Management (MPM) System, available at http://corventis.com/US/avivo.asp, copyright 2009, 2 pages.
Notice of Allowability dated Oct. 31, 2004; for U.S. Appl. No. 13/334,447; 10 pages.
South African Amendment dated Oct. 31, 2014; for South African Pat. App. No. 2014/04810; 10 pages.

(56) References Cited

OTHER PUBLICATIONS

PCT International Preliminary Report on Patentability of the ISA dated Jul. 31, 2014; for PCT Pat. App. No. PCT/US2013/020069; 6 pages.
PCT International Preliminary Report on Patentability of the ISA dated Jul. 31, 2014; for PCT Pat. App. No. PCT/US2013/020071; 6 pages.
Singapore Written Opinion dated Jul. 25, 2014; for Singapore Pat. App. No. 2013053244; 7 pages.
Russian Office Action (with English Summary) dated Oct. 28, 2014; for Russian Pat. App. No. 2014124988/20(040628); 3 pages.
Singapore Response to Written Opinion dated Nov. 18, 2014; for Singapore Pat. App. No. 2014/268260258W; 15 pages.
Australian Examination Report dated Oct. 28, 2014; for Australian Pat. App. No. 2012223646; 5 pages.
Singapore Response to Written Opinion dated Nov. 18, 2014; for Singapore Pat. App. No. 2014/269351479S; 21 pages.
Chinese Voluntary Amendment with PPH received Dec. 16, 2014; for Chinese Pat. App. No. 201280063960.1; 26 pages.
Chinese Voluntary Amendment with PPH received Dec. 17, 2014; for Chinese Pat. App. No. 201280063534.8; 25 pages.
Australian Response filed Dec. 16, 2014; for Australian Pat. App. No. 2012205515; 20 pages.
Korean Letter to Kim & Chang dated Dec. 5, 2014; for Korean Pat. App. No. 10-2013-7018317; 10 pages.
U.S. Response to 312 Amendment received Dec. 26, 2014; for U.S. Appl. No. 14/154,285; 7 pages.
Australian Patent Examination Report dated Nov. 18, 2014; for Australian Pat. App. No. 2012205516; 3 pages.
South African Notification of Acceptance dated Dec. 10, 2014; for South African Pat. App. No. 2013/05094; 1 pages.
Final Office Action dated Jan. 2, 2015; for U.S. Appl. No. 13/334,463; 48 pages.
Singapore Supplemental Search Report dated Dec. 8, 2014; for Singapore Pat. App. No. 2013065230; 8 pages.
Singapore Response to Written Opinion dated Dec. 31, 2014; for Singapore Pat. App. No. 2013053244; 19 pages.
European Response to Rule 161(2) and 162 EPC filed on Dec. 30, 2014; for European Pat. App. No. 12861028.4; 14 pages.
Singapore Request to Amend Application Before Grant filed on Jan. 15, 2015; for Singapore Pat. App. No. 11201404126W; 8 pages.
U.S. Appl. No. 14/308,881, filed Jun. 19, 2014, Gaines, et al.
Response with Terminal Disclaimer filed Jul. 30, 2014; to Office Action dated Jun. 20, 2014; for U.S. Appl. No. 13/334,447; 15 pages.
Response with Terminal Disclaimer filed Jul. 30, 3014; to Office Action dated Jun. 23, 2014; for U.S. Appl. No. 13/334,459; 13 pages.
Response filed Jul. 30, 3014; to Final Office Action dated Jun. 16, 2014; to U.S. Appl. No. 13/353,565; 22 pages.
Response filed Aug. 4, 2014; to Office Action dated May 27, 2014; for U.S. Appl. No. 13/334,463; 21 pages.
Mexican Reponse to Office Action received Jul. 29, 2014; for Mexican Pat. App. No. MX/a/2013/008157; 14 pages.
PCT International Preliminary Report on Patentability dated Jul. 3, 2014; for PCT Pat. App. No. PCT/US2012/068895; 10 pages.
Australian Notice of Acceptance dated Jan. 15, 2015; for Australian Pat. App. No. 2012206616 2 pages.
Singapore Search and Examination Report dated Dec. 23, 2014; for Singapore Pat. App. No. 2013053236; 4 pages.
Singapore Request to Amend Application Before Grant dated Jan. 16, 2015; for Singapore Pat. App. No. 11201404133R; 18 pages.
Australian Patent Examination Report No. 1 dated Nov. 11, 2014; for Australian Pat. App. No. 2013205134; 3 pages.
Singapore Amendment dated Sep. 12, 2014; for Singapore Pat. App. No. 11201403379U; 23 pages.
Japanese Notice of Reasons for Rejection dated Nov. 5, 2014; for Japanese Pat. App. No. 2013-556717; 8 pages.
Singapore Response to Written Opinion dated Nov. 18, 2014; for Singapore Pat. App. No. 2013065230; 21 pages.
South African Amendment dated Nov. 27, 2014; for South African Pat. App. No. 2013/05094; 9 pages.
Notice of Allowance dated Jan. 30, 2015; for U.S. Appl. No. 13/353,565; 23 pages.
European Response filed Feb. 2, 2015; for European Pat. App. No. 12860626.6; 14 pages.
Australian Response to Examiner's Report dated Feb. 10, 2015; for Australian Pat App. No. 2013205134; 13 pages.
Canadian Response to Examiner's Report dated Feb. 4, 2015; for Canadian Pat. App. No. 2823600; 50 pages.
Australian Patent Examination Report dated Feb. 2, 2015; for Australian Pat. App. No. 2012355639; 3 pages.
Chinese Response (including English translation) filed on Jul. 15, 2015 to Office Action dated Feb. 28, 2015; for Chinese Pat. App. No. 201280063534.8; 19 pages.
Japanese Voluntary Amendment (including English translation) filed on Jul. 21, 2015; for Japanese Pat. App. No. 2014-192221; 20 pages.
Mexican Memo Concerning the Official Action dated Jul. 9, 2015; for Mexican Pat. App. No. MX/a/2014/008678; 3 pages.
Russian Office Action dated Apr. 27, 2015 (including English translation) with European Arguments Amendments; for Russian Pat. App. No. 2013131828; 30 pages.
Japanese Office Action (including English translation) dated Jun. 29, 2015; for Japanese Pat. App. No. 2014-553309; 5 pages.
Japanese Office Action (including English translation) dated Jun. 26, 2015; for Japanese Pat. App. No. 2014-549109; 8 pages.
Australian Response dated Feb. 24, 2015; for Australian Pat. App. No. 2012223646; 24 pages.
Canadian Response dated Feb. 9, 2015; for Canadian Pat. App. No. 2823700; 29 pages.
Singapore Examination Report dated Feb. 26, 2015; for Singapore Pat. App. No. 2013053244; 12 pages.
Response filed Mar. 2, 2016; to Office Action dated Jan. 2, 2015; for U.S. Appl. No. 13/334,463; 24 pages.
Chinese Notification of First Office Action dated Feb. 28, 2015; for Chinese Pat. App. No. 201280063534.8; 10 pages.
Japanese Argument and Amendment (and English language summary) filed Mar. 25, 2015; for Japanese Pat. App. No. 2013-556171; 17 pages.
European Response filed Feb. 20, 2015; for European Pat. App. No. 14168075.7-1951; 20 pages.
Korean Response (and English language summary) dated Mar. 23, 2015; for Korean Pat. App. No. 10-2013-7018322; 46 pages.
Chinese Notification of First Office Action (including Claims in English) dated Mar. 20, 2015; for Chinese Pat. App. No. 201280063960.1; 23 pages.
Russian Response (including Claims in Engiish) filed Mar. 25, 2015; for Russian Pat. App. No. 2014124988; 15 pages.
Russian Response (inciuding Claims in English) flied Apr. 2, 2015; for Russian Pat. App. No. 2013131827; 14 pages.
Gao et al.; "Wireless Medical Sensor Networks in Emergency Response; Implementation and Pilot Results;" 2008 IEEE Conference on Technologies for Homeland Security; May 12, 2008; 6 pages.
Australian Patent Examination Report No. 1 dated Apr. 20, 2015; for Australian Pat. App. No. 2012355641; 6 pages.
Australian Patent Examination Report No. 1 dated Apr. 21, 2015; for Austrailan Pat. App. No. 2013210029; 2 pages.
Australian Notice of Acceptance dated Apr. 1, 2015; for Australian Pat. App. No. 2012223646; 2 pages.
Australian Response to Examiner's Report dated Apr. 27, 2015; for Australian Pat. App. No. 2012205516; 29 pages.
Chinese Office Action dated Apr. 20, 2015 (English translation) with Search Report; for Chinese Pat. App. No. 201260005240.X; 8 pages.
Canadian Office Action dated Jan. 29, 2015 with Search Report; for Canadian Pat. App. No. 2,828,436; 3 pages.
European Communication dated Apr. 27, 2016 with Claims; for European Pat. App. No. 14167899.5-1951; 4 pages.
Chinese Office Action dated Mar. 20, 2015 with Search Report for Chinese Pat. App. No. 201280063960.1; 15 pages.

(56) References Cited

OTHER PUBLICATIONS

English language summary of the Mexican Official Action received on May 26, 2015 for Mexican Pat. App. No. MX/a/2014/007436; 3 pages.
Japanese Notice of Appeal and Appeal Brief with English Claims filed on Jun. 8, 2015 for Japanese Pat. App. No. 2013-549532; 29 pages.
Singapore Invitation to Respond to Written Opinion and Search Report dated Jun. 12, 2015; for Singapore Pat. App. 11201403507X.
European Supplementary Search Report dated Jun. 10, 2015; for European Pat. App. No. 12861028.4; 8 pages.
Russian Office Action dated Jun. 2, 2015; for Russian Pat. App. No. 2014124988/07; 3 pages.
Singapore Invitation to Repond to Written Opinion and Search Report dated Jun. 4, 2015; for Singapore Pat. App. No. 11201403422P; 10 pages.
Russian Office Action dated Jul. 7, 2015 (with Engiish translation); for Russian Pat. App. No. 2013-140303; 7 pages.
Japanese Office Action dated Jun. 2, 2015 (with English translation); for Japanese Pat. App. No. 2013-556717; 9 pages.
Mexican Response with English language summary filed on Jun. 30, 2015 to Office Action dated Apr. 30, 2015; for Mexican Pat. App. No. MX/a/2014/007436; 28 pages.
Russian Notice of Allowance dated May 29, 2015 (with English translation); for Russian Pat. App. No. 2013-131827; 29 pages.
Korean Office Action dated Jun. 22, 2015 (with English translation); for Korean Pat. App. No. 10-2014-7016985; 11 pages.
Korean Office Action dated Jun. 22, 2015 (with English translation), for Korean Pat. App. No. 10-2014-7016960; 10 pages.
Korean Office Action dated Jun. 22, 2015 (with English translation); for Korean Pat. App. No. 10-2014-7016961; 10 pages.
Australian Notice of Acceptance dated Feb. 19, 2015; for Australian Pat. App. No. 2013205134; 2 pages.
Japanese Notice of Final Rejection dated Feb. 6, 2015; for Japanese Pat. App. No. 2013-549532; 5 pages.
Korean Notice of Preliminary Rejection (English translation) received Feb. 4, 2015; for Korean Pat. App. No. 10-2013-7018322; 10 pages.
Australian Response filed Oct. 29, 2015 to Examiner's Report dated Feb. 5, 2015; for Australian Pat. App. No. 2012355640; 13 pages.
Russian Response (with English summary) filed Nov. 11, 2015 to the Office Action dated Apr. 27, 2015; for Russian Pat. App. No. 2013131828; 13 pages.
Russian Notice of Allowance (with English translation) dated Oct. 5, 2015; for Russian Pat. App. No. 2014124988/07(040628); 20 pages.
Chinese Response to the Office Action (with English claims) dated Nov. 18, 2015; for Chinese Pat. App. No. 201380010091.0; 11 pages.
Canadian Office Action dated Aug. 3, 2015; for Canadian Pat. App. No. 2823600; 10 pages.
Japanese Office Action (with English translation) dated Oct. 30, 2015; for Japanese Pat. App. No. 2014-192221; 10 pages.
Canadian Examiner's Report dated Jul. 27, 2015; for Australian Pat. App. No. 2,859,360; 5 pages.
Singapore Response to Written Opinion and Amendments (English translation) filed on Nov. 6, 2015; for Singapore Pat. App. No. 11201403507X; 7 pages.
Singapore Response to Written Opinion and Amendments (English translation) filed on Nov. 4, 2015; for Singapore Pat. App. No. 11201403422P; 13 pages.
Japanese Petition with English summary dated Aug. 27, 2015; for Japanese Pat. App. No. 2013-549532; 3 pages.
Australian Notice of Acceptance dated Aug. 25, 2015; for Australian Pat. App. No. 2012355639; 2 pages.
European Communication with Search Report and Search Opinion dated Sep. 4, 2015; for European Pat. App. No. 13738949.0; 11 pages.
Singapore Examination Report and Search Report dated Jun. 18, 2015; for Singapore Pat. App. No. 11201403379U; 11 pages.

Australian Certificate of Grant dated Sep. 3, 2015; for Australian Pat. App. No. 2012205516; 1 page.
Singapore Response to Written Opinion dated Sep. 4, 2015; for Singapore Pat. App. No. 11201403378P; 12 pages.
European Communication dated Aug. 25, 2015; for European Pat. App. No. 13738062.2; 1 page.
Singapore Search Report and Written Opinion dated Jul. 9, 2015; for Singapore Pat. App. No. 11201404126W; 19 pages.
Korean Response to Office Action with English summary dated Aug. 21, 2015; for Korean Pat. App. No. 10-2014-7016961; 30 pages.
Korean Response to Office Action with English summary dated Aug. 21, 2015; for Korean Pat. App. No. 10-2014-7016960; 12 pages.
Japanese Response to Office Action with English summary dated Aug. 28, 2015; for Japanese Pat. App. No. 2014-553309; 15 pages.
Russian Response to Office Action with Engish summary dated Aug. 26, 2015; for Russian Pat. App. No. 2014124988; 14 pages.
Mexican Response to Office Action with English summary dated Aug. 25, 2015; for Mexican Pat. App. No. MX/a/2014/008678; 19 pages.
Korean Response to Office Action with English summary dated Aug. 21, 2015; for Korean Pat. App. No. 10-2014-7016985; 27 pages.
Chinese Response to Office Action with English summary dated Sep. 7, 2015; for Chinese Pat. App. No. 20128005240.X; 25 pages.
Singapore Written Opinion and Search Report dated Apr. 7, 2015; for Singapore Pat. App. No. 11201403378P; 10 pages.
European Search Report dated Aug. 17, 2015; for European Pat. App. No. 13738068.9; 9 pages.
Canadian Response dated Jul. 29, 2015 to Office Action dated Jan. 29, 2015; for Canadian Pat. App. No. 2828436; 21 pages.
Russian Response dated Jul. 28, 2015 to Office Action Jan. 31, 2015 with English summary and claims; for Russian Pat App. No. 2013140303; 23 pages.
Japanese Response dated Aug. 19, 2015 to Office Action dated Jun. 29, 2015; for Japanese Pat. App. No. 2014-553309; 12 pages.
European Search Report dated Aug. 18, 2015; for European Pat. App. No. 12860719.9; 11 pages.
Chinese Office Action dated Jul. 3, 2015 with Search Report; for Chinese Pat. App. No. 201380010091.0; 16 pages.
European Search Report dated Aug. 7, 2015; for European Pat. App. No. 13738062.2; 10 pages.
Anonymous: "Network Monitoring", Wikipedia, the free encyclopedia, Jan. 16, 2012, XPO55205397'retrieved from the Internet: https://en.wikipedia.org/wiki/Network_monitoring 3 pages.
Chinese Office Action dated Aug. 5, 2015 with Search Report; for Chinese Pat. App. No. 201280011025.0, 21 pages.
Chinese Office Action (with English translation) dated Aug. 14, 2015; for Chinese Pat. App. No. 201280063534.8; 19 pages.
Russian Office Action (with English translation) dated Dec. 10, 2015; for Russian Pat. App. No. 2014126451; 11 pages.
Canadian Office Action dated Oct. 6, 2015; for Canadian Pat. App. No. 2,861,110, 4 pages.
Chinese Notice of Grant dated Dec. 23, 2015 (with English translation); for Chinese Pat. App. No. 201380010091.0; 4 pages.
Singapore Response to Written Opinion dated Jan. 11, 2016; for Singapore Pat. App. No. 11201404126W; 10 pages.
Russian Decision to Grant (with English translation) dated Nov. 12, 2015; for Russian Pat. App. No. 2013131828/08(047587); 21 pages.
Australian Notice of Grant dated Dec. 17, 2015; for Australian Pat. App. No. 2012355639; 2 pages.
Korean Allowance Report dated Dec. 3, 2015; for Korean Pat. App. No. 10-2014-7016961; 2 pages.
Final Office Action dated Dec. 30, 2015; for U.S. Appl. No. 13/334,463, 57 pages.
Mexican Office Action dated Dec. 2, 2015; for Mexican Pat. App. No. MX/a/2014/008678; 11 pages.
Singapore Search and Examinatin Report confirming Notice of Grant dated Jan. 27, 2015; for Singapore Pat. App. No. 201306523-0; 13 pages.
Australian Second Examination Report dated Nov. 18, 2015; for Australian Pat. App. No. 2012355641; 4 pages.

(56) References Cited

OTHER PUBLICATIONS

Singapore Second Written Opinion/ Office Action dated Nov. 20, 2015; for Singapore Pat. App. No. 11201403378P; 6 pages.
Extented European Search Report dated Nov. 19, 2015; for European Pat. App. No. 12860626.6, 10 pages.
Rasid et al., "Bluetooth Telemedicine Processor for Multichannel Biomedical Signal Transmission via Mobile Cellular Networks", IEEE Transactions on Information Technology in Biomedicine, vol. 9, No. 1, Mar. 2005, 9 pages.
Japanese Response (with English sample arguments and claims) filed Dec. 1, 2015 to the Office Action dated Sep. 2, 2015; for Japanese Pat. App. No. 2014-547341; 21 pages.
Russian Final Office Action (with English translation) dated Nov. 9, 2015; for Russian Pat. App. No. 2014125728, 10 pages.
Mexican Office Action (English translation) dated Nov. 18, 2015; for Mexican Pat. App. No. MX/a/2014/008678, 11 pages.
Chinese Office Action (with English translation) dated Nov. 4, 2015; for Chinese Pat. App. No. 201280005240.X; 9 pages.
Korean Final Office Action (with English translation) dated Nov. 30, 2015; for Korean Pat. App. No. 10-2014-7016960, 5 pages.
Canadian Office Action dated Dec. 14, 2015; for Canadian Pat. App. 2,860,122; 4 pages.
Japanese Notice of Allowance (with English summary) dated Jan. 15, 2016; for Japanese Pat. App. No. 2014-553309; 4 pages.
Canadian Office Action dated Dec. 18, 2015; for Canadian Pat. App. No. 2,861,619; 4 pages.
Chinese Response to the Office Action dated Jan. 19, 2016; for Chinese Pat. App. No. 201280005240.X; 23 pages.
Japanese Office Action dated Oct. 2, 2015; for Japanese Pat. App. No. 2014-549006; 17 pages.
Australian Response filed Oct. 23, 2015 to Examiner's Report dated Apr. 20, 2015; for Australian Pat. App. 2012355641; 13 pages.
South African Notice of Acceptance; for South African Pat. App. No. 2014/04566; 1 page.
Israeli Response filed on Oct. 22, 2015 to the Notice under Section 18; for Israell Pat. App. No. 228111, 7 pages.
Russian Decision to Grant dated Sep. 2, 2015; for Russian Pat. App. No. 2013140303/08; 23 pages.
Chinese Amendment filed on Oct. 29, 2015; for Chinese Pat. App. No. 201280063534.8; 16 pages.
Australian Notice of Acceptance dated Dec. 1, 2015; for Australian Pat. App. No. 2012355640; 2 pages.
Chinese Office Action (with English translation) dated Nov. 27, 2015; for Chinese Pat. App. No. 201280083534.8; 16pages.
Canadian Examiner's Report dated Sep. 16, 2015; for Canadian Pat. App. No. 2861249; 4 pages.
European Amendment filed on Dec. 23, 2015, for European Pat App. No. EP12861028.4; 11 pages.
Japanese Amendment (with English translation) filed on Dec. 24, 2015; for Japanese Pat. App. No. 2014-549109; 14 pages.
Singapore Search Report and Written Opinion (English translation) dated Dec. 18, 2015; for Singapore Pat. App. No. 11201404133R; 11 pages.
Japanese Pre-Appeal Examination Report (English translation) dated Dec. 9, 2015, for Japanese Pat. App. No. 2013-556717; 3 pages.
Chinese Office Action (with English translation) dated Nov. 25, 2015; for Chinese Pat. App. No. 201280005209.6, 11 pages.
Canadian Office Action dated Oct. 14, 2015; for Canadian Pat. App. No. 2,823,700, 9 pages.
Canadian Examiners Report dated Jul. 14, 2015; for Canadian Pat. App. No. 2,859,854; 6 pages.
Japanese Office Action dated Sep. 4, 2015; for Japanse Pat. App. No. 2014-553340; 9 pages.
Japanese Response with English summary and claims filed on Sep. 30, 2015 to Office Action dated Jun. 30, 2015; for Japanese Pat. App. No. 2014-549110; 23 pages.
Japanese Notice of Appeal, Appeal Brief and Amendment filed on Oct. 1, 2015; for Japanese Pat. App. 2013-556717; 10 pages.
Korean Response with English summary and claims filed on Sep. 18, 2015 to Office Action dated Jul. 21, 2015; for Korean Pat. App. No. 10-2014-7017076; 16 pages.
Israeli Response with English summary and claims filed on Oct. 8, 2015 to Office Action dated Jun. 8, 2015; for Israeli Pat. App. No. 227269; 7 pages.
Israeli Response with English summary and claims filed on Oct. 8, 2015 to Office Action dated Jun. 8, 2015; for Israeli Pat. App. No. 227455; 5 pages.
Korean Office Action dated Sep. 14, 2015; for Korean Pat. App. No. 10-2014-7022485; 12 pages.
Bietsas et al., "A Simple Cooperative Diversity Method Based on Network Path Selection", IEEE Journal on Selected Areas in Communications; vol. 24, No. 3, Mar. 2006, pp. 659-672.
Chinese Response filed on Oct. 9, 2015 to the Office Action dated Mar. 20, 2015; for Chinese Pat. App. No. 201280063960.1; 16 pages.
Japanese Official Action (with English translation) dated Jul. 30, 2015; for Japanese Pat. App. No. 2014-549110.
Korean Notice of Preliminary Rejection (with English summary) dated Jul. 21, 2015; for Korean Pat. App. No. 10-2014-7017076; 4 pages.
Australian Response to Examiner's Report dated Jul. 22, 2015; for Australian Pat. App. No. 2012355639; 23 pages.
Japanese Pre-Appeal Examination Report (English translation) dated Jul. 6, 2015; for Japanese Pat. App. No. 2013-549532; 6 pages.
Japanese Patent Application No. 2014-549110 Notice of Allowance dated Feb. 16, 2016, including English Summary Form, 5 pages.
Korean Patent Application No. 10-2014-7017076 Office Action dated Jan. 30, 2016, including English Summary, 8 pages.
Japanese Patent Application No. 2014-192221 Office Action dated Oct. 30, 2015, including English Summary, 11 pages.
Korean Patent Application No. 10-2014-7016985 Letters Patent dated Jan. 7, 2016, including English Summary, 3 pages.
Chinese Patent Application No. 201280063960.1 Office Action dated Jan. 22, 2016, including English Summary, 11 pages.
Singapore Patent Application No. 11201403422P Invitation to Respond to Written Opinion dated Jan. 19, 2016, 5 pages.
Canadian Patent Application No. 2859360 Response to Office Action dated Jan. 27, 2016, 40 pages.
Japanese Patent Application No. 2014-549109 Notice of Allowance dated Feb. 1, 2016, including English Summary, 5 pages.
European Patent Application No. 13738062.2-1952 Response to Office Action filed Feb. 29, 2016, 15 pages.
Japanese Patent Application No. 2014-553340 Response to Office Action filed Mar. 2, 2016, including English translation of amended claims, 27 pages.

\* cited by examiner

460

Diagnostics

1. A progression of testing each of these with pass/fail:
   1. Accuracy
   2. AC Power
   3. Battery
   4. Motor
   5. Sensor
   6. Memory
   7. Radio
   8. Buzzer
   9. ADC
   10. Feed/Flush Control
   11. Display
   12. Failsate 2. Also, show error statistics:
   1. System Error (x per hours of run-time)
   2. Rotor Error (x per hours of run-time)
   3. Feed Error (x per hours of run-time)
   4. Flush Error (x per hours of run-time)
   5. Pump Set Dislodged Error (x per hours of run-time)

3. Version Number

461 — (list 1)
462 — (list 2)
463 — (version)

FIG. 4 (c)

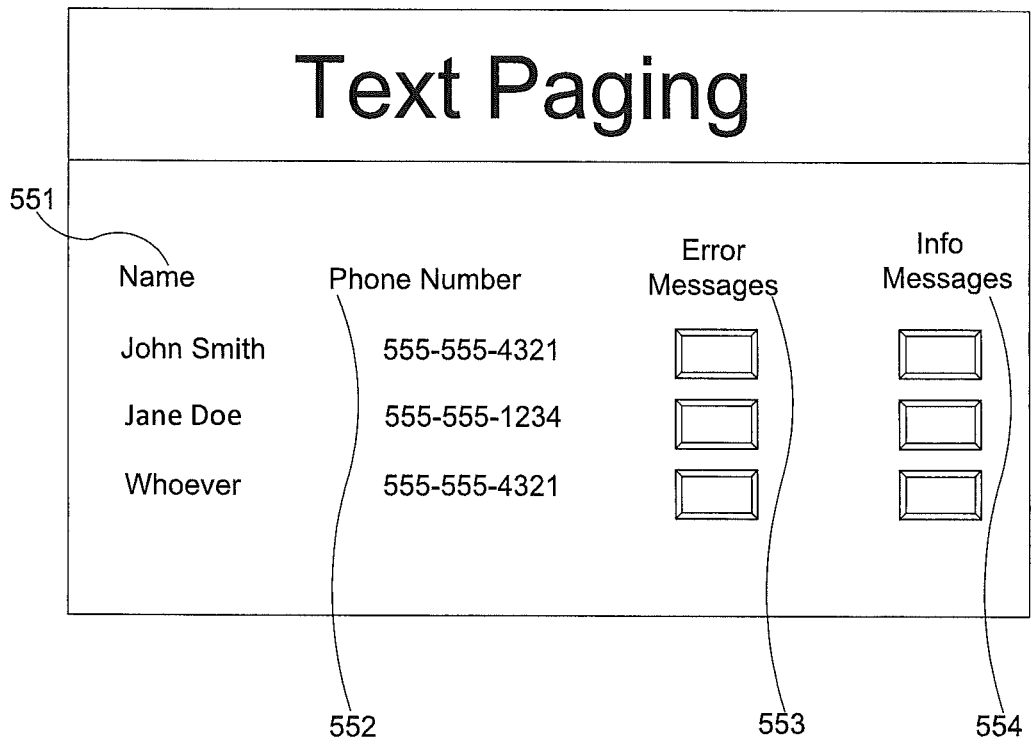
FIG.5 ( b )

ially confidential patient information and associated medical device status only to authorized personnel, and of retaining such information for historical purposes.

REMOTE MONITORING SYSTEMS AND METHODS FOR MEDICAL DEVICES

RELATED APPLICATIONS

This application is a continuation-in-part patent application of U.S. application Ser. No. 13/037,886, filed Mar. 1, 2011, entitled "Remote Monitoring Systems For Monitoring Medical Devices Via Wireless Communication Networks," which is incorporated by reference in its entirety herein for all purposes.

FIELD OF THE INVENTION

The present application is directed to a remote monitoring system for monitoring medical devices in communication with a wireless communication network, and more particularly, to a remote monitoring system having a plurality of monitoring devices for monitoring medical devices that communicate with the wireless communication network via one or more wireless relay modules and a wireless relay network.

BACKGROUND OF THE INVENTION

In critical care and home care health service centers, including hospitals, clinics, assisted living centers and the like, care giver-patient interaction time is at a premium. Moreover, response times by care givers to significant health conditions and events can be critical. Systems of centralized monitoring have been developed to better manage care giver time and patient interaction. In such systems, physiological data from each patient is transmitted to a centralized location. At this centralized location, a single or small number of technicians monitor all of this patient information to determine patient status. Information indicating a patient alarm condition will cause the technicians and/or system to communicate with local care givers to provide immediate patient attention, for example via wireless pagers and/or cell phones, and/or by making a facility-wide audio page.

Implementing such centralized monitoring systems using wireless networks may present a number of difficulties. In order to effectively monitor patient status using information provided by a variety of medical devices that may be dynamically assigned to patients in a variety of rooms and on a variety of floors in a facility, it would be desirable to establish communications between the medical devices and the centralized location by means of a local area network such as, for example, a "WiFi" network based on IEEE 802.11 standards. However, as such networks are typically already in place in facilities to support a variety of other functions (for example, physician access to electronic medical records (EMRs), facility administrative systems and other functions), it is often undesirable to secure sufficient local area network access for the purpose of providing centralized monitoring. Moreover, when a patient is located remotely from a critical care health service center (for example, at home), access to traditional local area network facilities such as a WiFi network may be unavailable or not sufficiently reliable to support critical care monitoring applications.

For improved efficiencies in centralized monitoring of critical care and home care health service centers, it may be desirable to provide a single "off-site" centralized monitoring location for monitoring several geographically-dispersed critical care health service centers.

As an alternative to conventional WiFi or IEEE 801.11-based local area networks, ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety. As compared to present IEEE 802.15.1 Bluetooth wireless personal area networks, for example, ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. As a consequence, such networks are suitable for on-site communications with medical devices, but unusable for centralized monitoring locations located off-site.

Therefore, a hybrid system may be employed in which one or more wireless personal area networks are configured to facilitate on-site communications between medical devices and one or more wireless relay modules which are further configured to communicate with off-site centralized monitoring systems (for example, via a wireless wide-area network (WWAN) such as a mobile telephone data network, for example, based on a Global System for Mobile Communications (GSM) or Code Division Multiple Access (CDMA) cellular network or associated wireless data channels). Such a relay module and system are respectively described in the related patent applications entitled "Wireless Relay Module for Remote Monitoring Systems," U.S. application Ser. No. 13/006,769, filed Jan. 14, 2011 and "Medical Device Wireless Network Architectures," U.S. application Ser. No. 13/006,784, filed Jan. 14, 2011) which have been incorporated by reference herein for all purposes.

In accordance with applicable patient data privacy provisions of the Health Insurance Portability and Accountability Act of 1996 (HIPAA), communication of information between the monitored medical devices and the central monitoring location must be done securely, and medical device and associated patient information must be made available only to personnel accessing the centralized monitoring systems who are in possession of the appropriate access credentials. In order to be viable, the centralized monitoring system must also be capable of recognizing medical device information indicating an alert condition requiring response by on-site or other specialized personnel and reaching those on-site or specialized personnel to report the alert condition in a timely fashion.

Thus, it would be desirable to provide a remote, centralized medical information monitoring system that communicates over a wireless network of wide reach (for example, a wireless wide area network) with one or more critical care and/or home care health service centers via one or more wireless relay modules at each site, where the wireless relay modules relay communications provided by on-site medical devices over a wireless local area network or wireless personal area network. It would further be desirable for the centralized medical information monitoring system to be capable of also configuring medical devices according to associations with individual sites and patients, of logging communications from medical devices, of displaying medical device data to users of the centralized medical information monitoring system who are able to provide sufficient credentials, and of recognizing medical device alert conditions and reporting these conditions to responsible personnel in a timely fashion.

SUMMARY OF THE INVENTION

The present invention is directed to a remote monitoring system and method for monitoring the status of a plurality of medical devices located remotely from the monitoring system at a patient care or home care facility. In accordance with one embodiment of the invention, one or more medical devices (including but not limited to respirators, enteral feeding devices, pulse oximeters, blood pressure monitors, pulse monitors, weight scales and glucose meters) are provided at a patient care or home care facility. An interface circuit is coupled to each medical device, and is configured for communicating with one of a plurality of the wireless relay modules via a wireless relay network. The wireless relay modules are further configured to communicate with the remote monitoring device over an internet-accessible wireless communication network, and preferably, a wireless wide-area network (WWAN) such as a mobile telephone data network including (for example, based on a Global System for Mobile Communications (GSM) or Code Division Multiple Access (CDMA) cellular network or associated wireless data channels). Also, for compliance for example with HIPAA regulations, communications over each of the wireless networks are preferably conducted securely.

The remote monitoring system and method includes a device integration server in communication with the wireless relay modules for receiving data packets from the wireless relay modules including information provided by the medical devices. This information includes identification of an associated medical device and may include data of the medical device, and is preferably encrypted or otherwise securely transmitted, for example, in compliance with HIPAA patient data privacy provisions. In addition, the information may include encrypted or otherwise securely transmitted patient identification information, which in addition may preferably be coded in its unencrypted state to avoid any reference to the patient's identity.

The remote monitoring system also includes a data management system including a secure device web server and a device control database, and an outbound web server. The data management system is configured to log information provided to the device integration server concerning the medical devices. The outbound web server (alternatively referred to as "web server" herein) is configured to provide webpages including the data of the medical devices for display on a first and second remote monitoring devices, subject to authentication of an associated data request originating from the monitoring device. The second monitoring device may advantageously be for use by a relative of the patient, such as a parent, caregiver or nurse, who may be located proximate or remote to the patient.

BRIEF DESCRIPTION OF THE DRAWINGS

The invention will become more readily apparent from the Detailed Description of the Invention, which proceeds with reference to the drawings, in which:

FIG. 5(b) illustrates an exemplary screen display for selecting a recipient for receiving an alert message according to the method of FIG. 5(a)

DETAILED DESCRIPTION OF THE INVENTION

Reference will now be made in detail to exemplary embodiments of the invention, including the best modes contemplated by the inventors for carrying out the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1-6.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1:
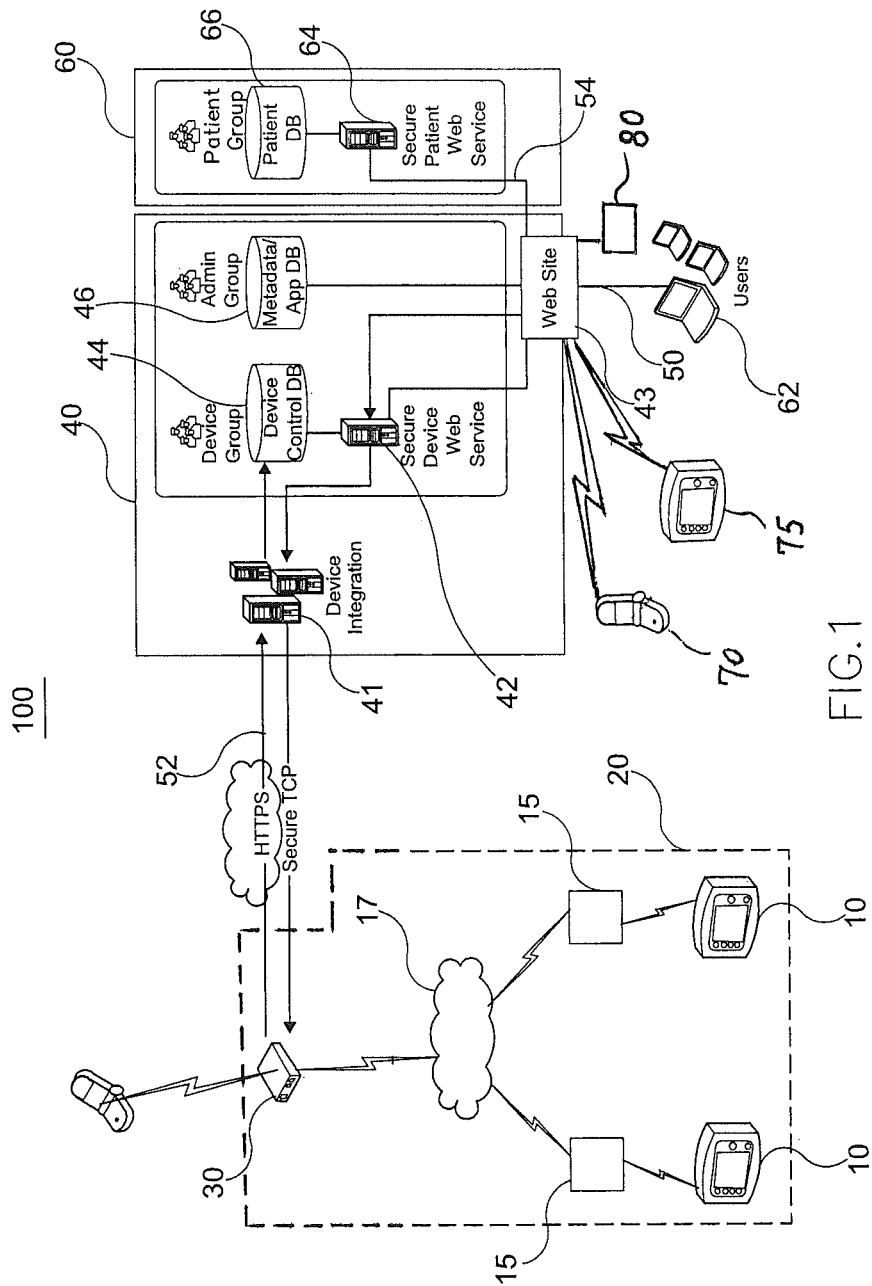
FIG. 1 presents a block diagram of an exemplary remote monitoring system for remotely monitoring medical devices according to the present invention.

A diagram of an exemplary system 100 for monitoring medical devices in accordance with the present invention is illustrated in FIG. 1. For example, one or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, or a personal enclosure (for example, a backpack) that may be attached to or worn by an ambulatory patient. Examples of medical devices include, but are not limited to, include ventilators, urology devices, energy delivery devices, pulse oximeters, predictive thermometers, tympanic thermometers, patient electrodes, and food pumps.

Associated with each medical device 10 is an interface circuit 15 that includes a transceiver having one or more of a transmitter and/or a receiver for respectively transmitting and receiving signals in a facility-oriented wireless network 17 such as, for example, a Low-Rate Wireless Personal Area Networks or "LR-WPAN," ZIGBEE network or another low-power personal area network such as a low power Bluetooth network, existing or presently under development or consideration. See, e.g., Houda Labiod et al., *Wi-Fi, Bluetooth, Zigbee and WiMax*, Springer 2010, which is incorporated by reference herein in its entirety. It should be understood that interface circuit 15 may be contained within or disposed external to medical device 10 in accordance with the present invention.

Also provided within the patient facility 20 are one or more relay modules 30. Each relay module 30 includes a first transceiver for receiving signals from and transmitting signals to the interface circuits 15 in the facility-oriented wireless network 17, and further includes a second transceiver for wirelessly transmitting signals to and receiving signals from an access point 40 via a wireless wide-area network ("WWAN") 52. Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union Radiocommunication Sector (ITU-R). See, e.g., Vijay Garg, *Wireless Communications & Networking*, Morgan Kaufmann 2007, which is incorporated by reference herein in its entirety. For compliance with HIPAA regulations, communications over each of the facility-oriented wireless network and WWAN are preferably conducted securely using, for example, a Secure Sockets Layer (SSL) protocol or a Transport Layer Security (TLS) protocol or other cryptographic protocols.

As illustrated in FIG. 1, the access point 40 useable with the present invention includes an inbound server ("device integration server") 41 that incorporates or otherwise has access to a transceiver for communicating with the relay modules 30 over the WWAN. Medical device data, medical device identifier, and/or patient identifier received by the device integration server 41 over the WWAN is forwarded to a secure device web server 42, which is configured for example to log the received data in association with identification information of the associated medical devices in a device control database 44. "Medical device data" as generally used herein means data from or about the medical device including, for example, medical device identification, medical device software, medical device settings or status information (including alarm information and/or alarm priority), patient identification information, patient personal identification number(s) "PIN(s)", patient prescriptions, and/or patient medical and/or physiological data as is collected, produced and/or generated by at least one of the medical device and patient identification device; as well as wireless relay network information such as location or status information.

An outbound web server 43 is configured, for example, to receive and qualify data retrieval requests submitted by one or more of first remote monitoring devices 62 over a broad-band network 50 (for example, over the Internet), and/or second remote monitoring devices 70, 75 over a wired or wireless wide area network. It is advantageous for such requests be made in an encrypted format. Suitable encryption formats useable for such requests may include, for example, formats compliant with the HIPAA regulations described above. For each qualified request, the outbound web server 43 requests associated medical device data or portions thereof to be retrieved from the device control database 44 via the secure device web server 42, requests associated program data for constructing a display page from a metadata and applications database 46, and requests associated patient data to be retrieved from a patient database 66 provided in a patient care database node 60 over a secure link 54 via a secure patient web server 64. The secure link 54 can be implemented, for example as another WWAN using a SSL protocol or a TLS protocol. By separating medical device data and patient data to be respectively stored and managed by access point 40 and patient care database node 60, certain economies of scale can be achieved by configuring the access point 40 to support a number of different patient care facilities each maintaining its own secure patient care database node 60 to ensure privacy and control of its associated patient data.

In this case, for example, a third party service provider may host the access point 40 to simultaneously support a number of distinct patient and/or home care facilities, thereby eliminating the need for each of these facilities to configure and maintain their own private access point facilities and providing hosting service to each facility that are likely far less than the costs of configuring and maintaining dedicated access point facilities by each care facility provider. It should be noted however that, consistent with principles of the present invention, access point 40 and patient care database node 60 may nevertheless be integrated into a single access point or node (for example, by a provider of a very large-scale facility provider monitoring many hundreds or thousands of patients). In either case, and as further described herein, the outbound web server 43 provides an interface for authenticated clinicians or other monitoring personnel to retrieve patient and medical device data from each of the patient care database node 60 and the access point 40 in a convenient and transparent manner such that the details of the configurations and operation of the access point 40 and patient care database node 60 are of no consequence to the clinicians or other monitoring personnel.

The first remote monitoring devices 62 are intended to be used by healthcare providers such for example, clinicians, physicians, technicians, nurses and other healthcare specialists monitoring patients associated with medical devices 10. Suitable first remote monitoring devices 62 may include, for example, desktop or laptop computers, tablet computer smart or other mobile phones, or other fixed or portable display devices. The second remote monitoring devices 70, 75 are advantageously intended to be used by caregivers and/or relatives of the patient such as parents, located proximate the patient such as in a homecare environment or small healthcare facility, or nurses at a larger healthcare facilities, e.g., hospitals. Suitable second remote monitoring devices 70, 75 likewise may include, for example, desktop or laptop computers, tablet computer, smart or other mobile phones, or other fixed or other portable communication devices.

In addition, the outbound web server 43 is depicted coupled to a network status server 80, which monitors the status of the facility-oriented wireless network 17 and associated medical devices 10. The network status server 80 is intended to provide status information concerning the facility-oriented wireless network 17 and associated medical devices 10 to the outbound web server 43. Exemplary status information concerning the facility-oriented wireless network 17 includes, for example, signal strength, data rates, particular transmission time stamps between modules comprising the network 17, number active relay modules in the network 17, unique identifier number for a particular relay module of the network 17.

The network status server 80 may be implemented in hardware or software running on an application specific or general purpose processor or computer, as part of or separate from the outbound web server 43. In addition, the network status server 80 is shown coupled to the outbound web server 43 for ease of illustration and discussion purposes only. The network status server 80 may be coupled to any component or network of the access point 40 or facility-oriented wireless network 17 in accordance with the invention.

In FIG. 1, upon retrieving the requested medical device data and patient data from the patient care database node 60, the outbound web server 43 then proceeds to format and transmit the retrieved medical device data and patient data (and/or provide status information concerning the facility-oriented wireless network 17 and associated medical devices 10) as respective webpages or other formats for display by corresponding first and second remote monitoring devices 62, 70, 75 according to the retrieved program data. It is possible for the webpages or other formatted information for display to include the same or differing content and format for the intended remote monitoring device user depending upon the retrieved program data. For example, the detailed medical device data provided to and displayed on a first remote monitoring devices 62 for a clinician may differ from the less detailed information provided to and displayed on a second remote monitoring devices 70 monitored by a parent or visiting nurse or other healthcare professional in a home-care environment. The status information concerning the facility-oriented wireless network 17 and associated medical devices 10 may advantageously be provided to first and/or second remote monitoring devices 62, 70 and 75 in the same or different encrypted formats as may be deemed appropriate.

In addition, and as will be further described herein, the device integration server 41 of FIG. 1 is configured to transmit information and commands to the relay modules 30, for example, for transmitting medical device or alert messages to other WWAN-reachable nodes (for example, cellular telephones of emergency attendants), and/or transmitting operating commands and/or software or firmware updates to the medical devices 10 via the interface circuits 15 and facility-oriented wireless network 17.

Further, in addition to monitoring and sending commands to medical devices, the device integration server 41 may also be configured to receive and analyze patient metric information from the secure patient web server 64 via the outbound web server 43 and secure device web server 42, or by an alternate and direct secure data link to the secure patient web server 64 in order to prevent unsafe medical device usage based upon the patient metrics information. It is possible for a database (not depicted) accessible, for example, by the device integration server 41 and/or device web server 42, to store various safe and unsafe operating parameters and conditions for performing such analysis. In this manner, the device integration server 41 would function as an additional failsafe for preventing operating errors that could result in patient harm.

For example, in the case that the patient metric information indicates that an enteral feeding pump is associated with a neonate, the device integration server 41 may act, for example, to (1) discard remote monitoring commands programming large bolus or excessive feeding rates that could be harmful to a young child; and (2) provide a warning message or other notification to the user of the likely unsafe usage condition that may result by implementation of such comment. Alternatively, if the patient metric information indicates that a specific feeding rate or bolus amount has been prescribed by a doctor or clinician, then the device integration server may act to discard remote monitoring commands programming a rate or bolus that deviates from the prescription.

Figure 2:
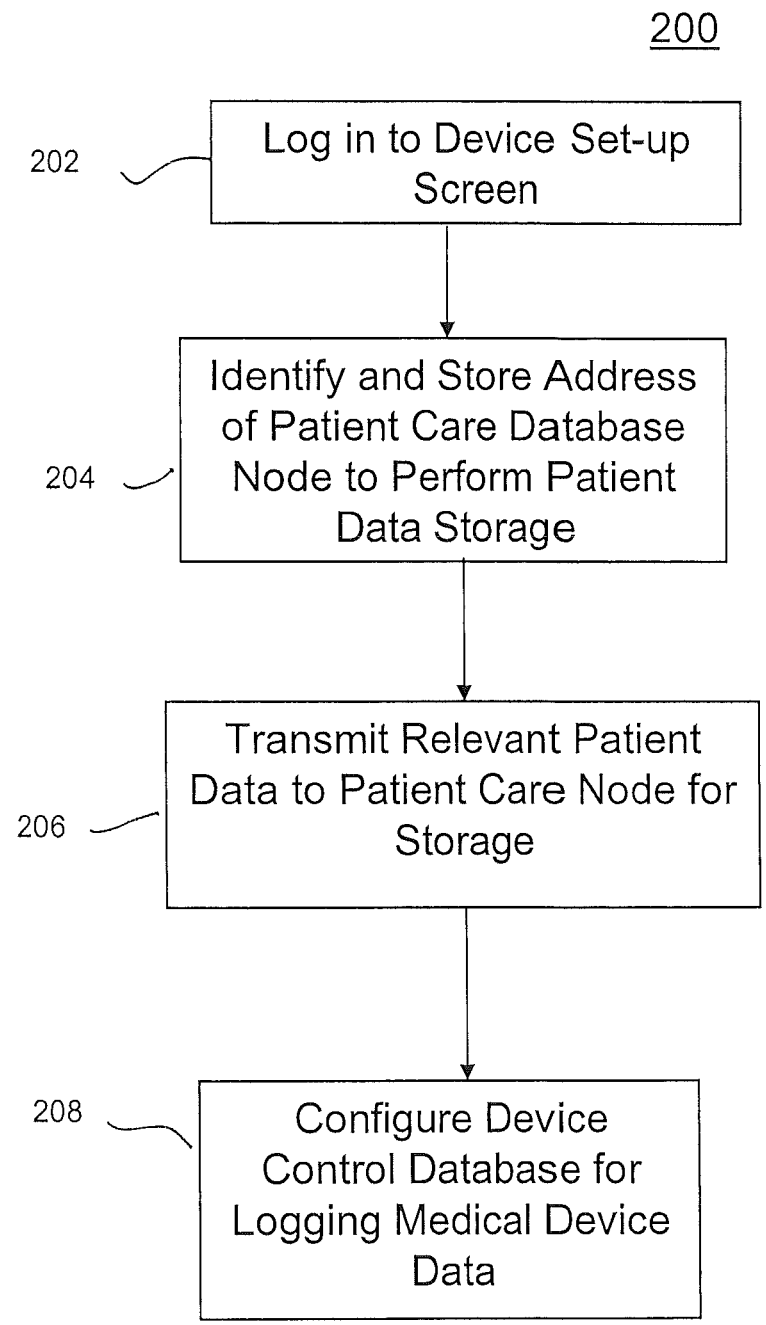
FIG. 2 presents a flow diagram illustrating an exemplary method for registering medical devices with the remote monitoring system according to FIG. 1.

FIG. 2 illustrates a flow diagram of one exemplary method 200 in accordance with the invention for registering medical devices 10 with the system 100 of FIG. 1. The method 200 begins at step 202, at which an authorized technician or other personnel having access to one of the remote monitoring devices 62, 70, 75 provides authenticating credentials (for example, a recognized log-in and password) to the outbound web server 43, and the web server responds by transmitting a device set-up screen to the remote monitoring device 62, 70, 75 requesting medical device identifying information and associated patient identifying information.

At step 204, the outbound web server 43 preferably queries the metadata and application database 46 according to one or more of identifying information for the technician and/or identifying information for the patient to identify an associated patient care database node 60 from a plurality of patient care database nodes for the patient and record a destination address for the associated patient care database node 60 in the metadata and application database 46 in association with the identifying data for the medical device 10 and/or identifying information for the patient. Identifying information for the patient is preferably generated anonymously (for example as a random number), and transmitted at step 206 to the patient care database node 60 for association with securely-stored patient identifying information. At step 208 of the method 200 of FIG. 2, the outbound web server 43 requests that the secure device web server 42 assign an area of the device control database 44 for logging associated medical device data for the medical device 10 as it is received by the device integration server 41, such that it can be later retrieved by the outbound web server 43 upon receiving an authorized request from an authenticated user operating one of the remote monitoring devices 62, 70, 75.

It should be readily understood by one skilled in the art that step 204 of method 200 for identifying and storing the address of the patient care database node 60 may be omitted in accordance with the invention if a single patient care database node is utilized with system 100 of FIG. 1.

Figure 3:
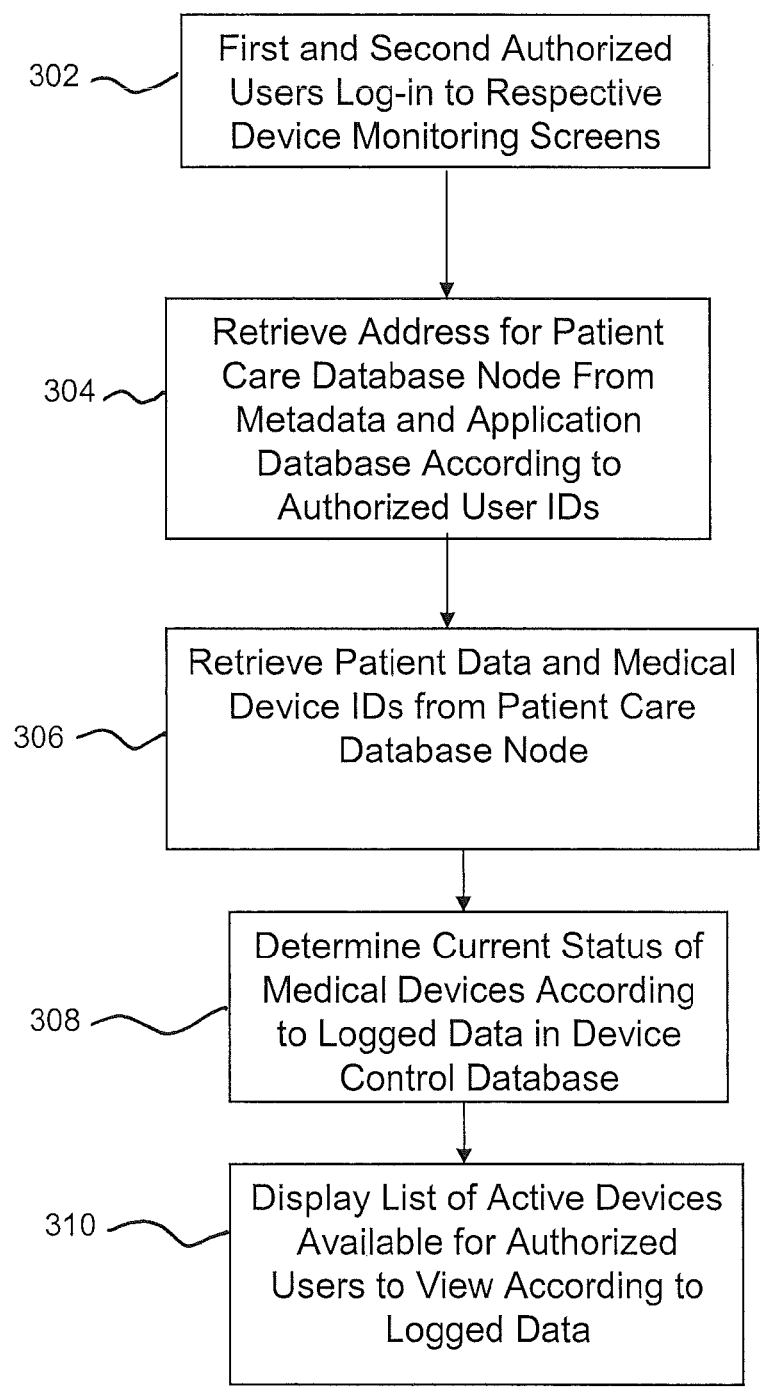
FIG. 3(a) presents a flow diagram illustrating an exemplary method for retrieving and viewing medical data via the remote monitoring system according to FIG. 1.
FIGS. 3(b)-3(d) illustrate exemplary screen displays for retrieving and viewing the medical data according to the method of FIG. 3(a)
Figure 3:
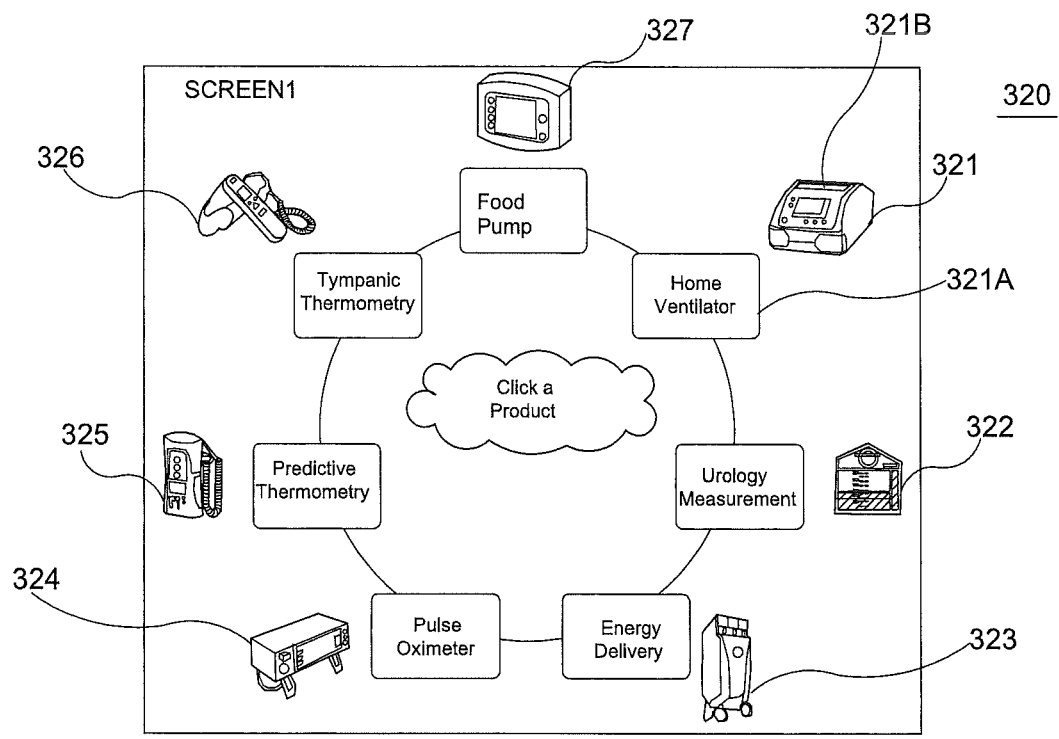
Figure 3:
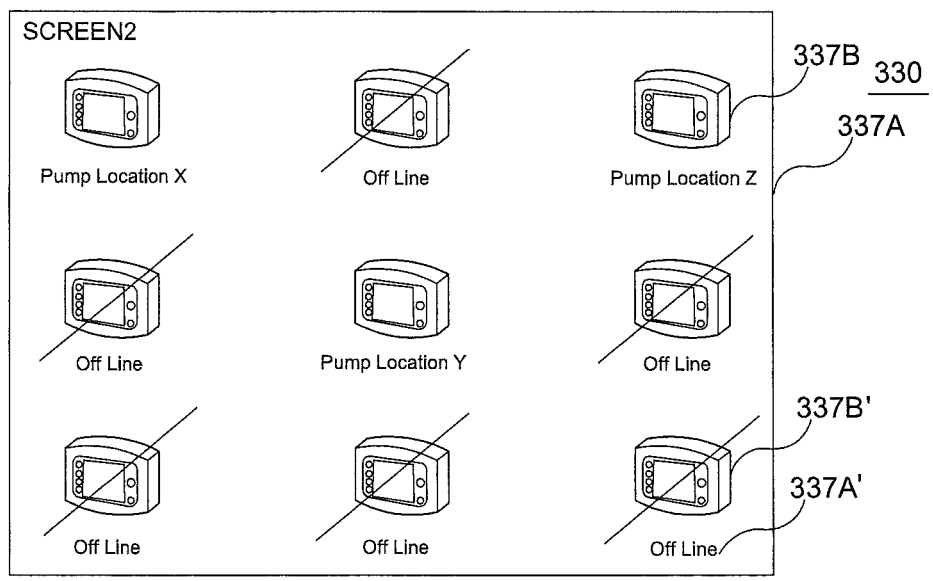
Figure 3:
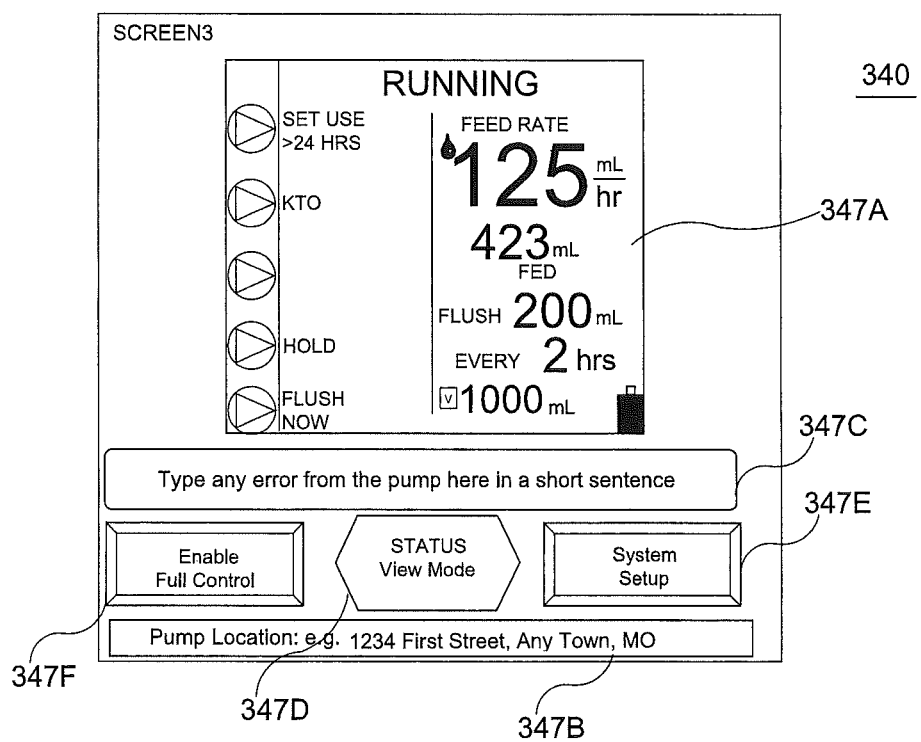

FIG. 3(*a*) presents a flow diagram illustrating one exemplary method 300 in accordance with the invention for retrieving and viewing medical device data on a remote monitoring device 62, 70, 75 for a registered medical device 10 according to the system of FIG. 1. The method 300 begins at step 302 with a first authorized user having access to one of the first remote monitoring devices 62 provides authenticating credentials (for example, a recognized log-in and password) to the outbound web server 43. In addition, in step 302, a second authorized user having access to one of the second remote monitoring devices 70, 75 likewise provides respective authenticating credentials to the outbound web server 43

At step 304, based on verification of the authenticating credentials of the first and second authorized users, the outbound web server 43 queries the metadata and applications database 46 to identify the address of patient care database node(s) 60 to which the respective first and second authorized users are entitled to obtain access, and at step 306, requests data from the patient care database node 60 relating to at least one identified patient for which the first and second user are respectively authorized to view medical device data, including for example a listing of medical devices 10 which are presently associated with the identified patient, and/or status information of the facility-oriented network 17. It should be readily understood that different authenticated users will likely have different levels of sophistication and skill for which a corresponding access level may be associated with their authentication account or status which may further be used, for example, to limit or expand the type and/or extent of medical device data that may be transmitted to the remote monitoring devices for such authenticated users.

At step 308 of the method 300 of FIG. 3(*a*), the outbound web server 43 queries the device control database 44 via the secure device web server 42 for status information to determine which of the listed medical devices are presently active according to the data logged by the device control database 44. It should be noted that one or more of a medical device 10, its associated interface device 15, an associated wireless relay module 30 and/or the device integration server 41 may be programmed to provide data from the medical device 10 to the device integration server 41 at predetermined, preset intervals or otherwise, which can then be provided to server 43 in response to inquiries therefrom.

Upon obtaining the status information, the outbound web server 43 prepares respective display pages with encrypted medical device data, according for example to display information retrieved from the metadata and applications database 46, to display listings of medical devices 10 available for monitoring by respective authorized users at the remote monitoring devices 62, 70, 75. FIG. 3(*b*) presents a first exemplary screen display 320 to the remote monitoring devices 62, 70, 75 that provides an array of medical devices 10 available for monitoring according to device type. For example, in the screen display 320 of FIG. 3(*b*), available device types include ventilators 321, urology devices 322, energy delivery devices 323, pulse oximeters 324, predictive thermometers 325, tympanic thermometers 326 and food pumps 327. Each of the device types 321-327 in FIG. 3(*b*) is presented with an identifying label (for example, label 321A) and an identifying image (for example, image 321B) for ease of recognition.

Once a device type is selected by a user (for example, in response to an associated mouse-over or mouse-click executed by the authorized user), a second exemplary screen display 330 as illustrated by FIG. 3(*c*) may preferably be transmitted by the outbound web server 43 for display at the remote monitoring devices 62, 70 or 75. In the display 330, labels 337A are provided in association with images 337B in order to identify individual food pumps (for example, by patient and/or by logical or physical location). Medical devices 10 that are unavailable may for example preferably be depicted with a label 337A' ("Off Line") and an image 337B' (depicting the device with a slash or cross applied over the image or shaded or shadowed) that distinguish the unavailable medical devices 10 from available medical devices 10.

Once an individual device is selected by the first or second user (for example, once again, in response to an associated mouse-over or mouse-click executed by the authorized user), a third exemplary screen display 340 as illustrated by FIG. 3(*d*) may preferably transmitted by the outbound web server 43 for display at the corresponding remote monitoring device 62, 70, 75. In the display 340, for example, device information of the medical device 10 (in this case, a food pump) is displayed in a screen 347A preferably recreating a current screen generated and displayed by the medical device 10. In addition, the screen display 340 includes any of a panel 347B providing identifying information for the medical device 10 (in this case, a pump location), a panel 347C for displaying a message indicating a current error condition of the pump, and an icon button 347D for selecting an alternate "status" mode of the screen display 340. The screen display 340 also includes a control icon button 347E for selecting a system set-up screen display, and a control icon button 347F for enabling device control from the remote monitoring device 62. For example, upon selecting the control icon 347F, the screen display 340 may preferably be refreshed to include the medical devices screen 347A and one or more operable buttons that mimic the appearance of control buttons on the medical device. The control button features are described in greater detail below in relation to FIGS. 4(*b*) and 4(*c*).

It should be readily understood that exemplary computer screen images 320, 330 and 340 and corresponding navigation depicted by FIGS. 3(*b*), 3(*c*) and 3(*d*) are for illustration purposes only and that many other user screen images displays and interface tools may be utilized for carrying out the present invention including, for example, computer screens that depict accessible medical devices by other means than device type as illustrated in FIG. 3(*b*). For example, as a suitable alternative to the screen image 340 of FIG. 3(*d*) that conveys information from a single medical device, it is possible to implement displays that provide information from multiple medical devices. In addition, it should be readily understood that the outbound web server 43 will preferably be operable to prepare display pages with encrypted medical device data for display on any of a wide variety of display devices (including, for example, workstations, personal computers, tablet devices including tablet computers, and display-based mobile devices including personal digital assistants, smartphones, portable game systems and the like.

It should also be readily understood that the computer screen images to be available to first and second users of the first and second remote monitoring devices may be different depending upon whether such user is a clinician, nurse, patient relative or other caregiver, i.e., dependent on level of entitlement of the particular authorized user. For example, a display for a clinician at a first remote monitoring device 62 may enable the clinician to adjust the settings of a subject medical device 10, in contrast to a display for a second remote monitoring device 70, 75 used by a patient relative, which depicts only fundamental information from the medical device data with no option for the patient relative to adjust the medical device settings via the second remote monitoring device 70, 75. Likewise, different encryption methods or formats may be employed for medical device data transmitted to the first remote monitoring device 62 than the second remote monitoring device 70, 75.

Figure 4A:
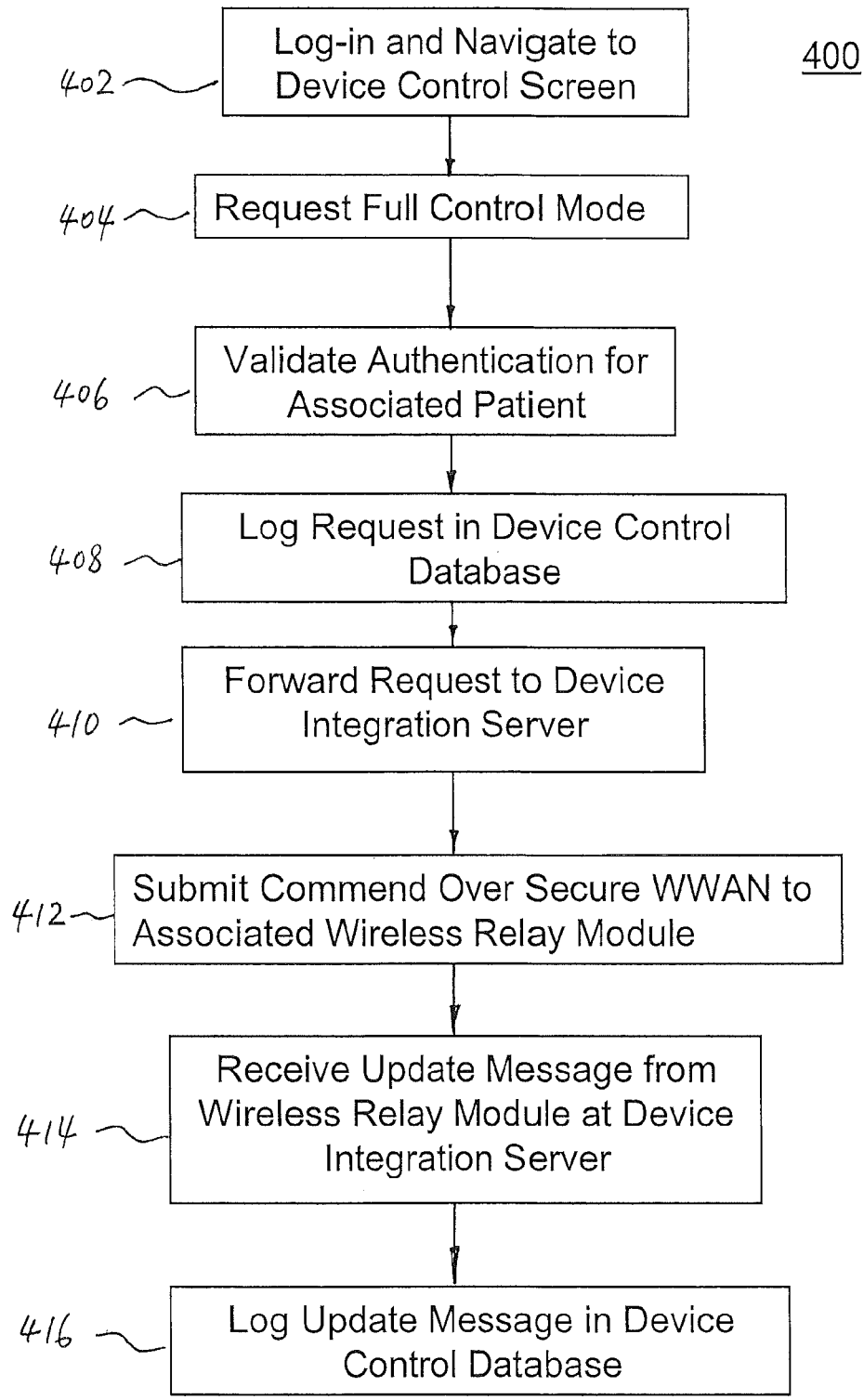
FIG. 4(a) presents a flow diagram illustrating an exemplary method for issuing a command to a medical device via the remote monitoring system according to FIG. 1.
Figure 4:
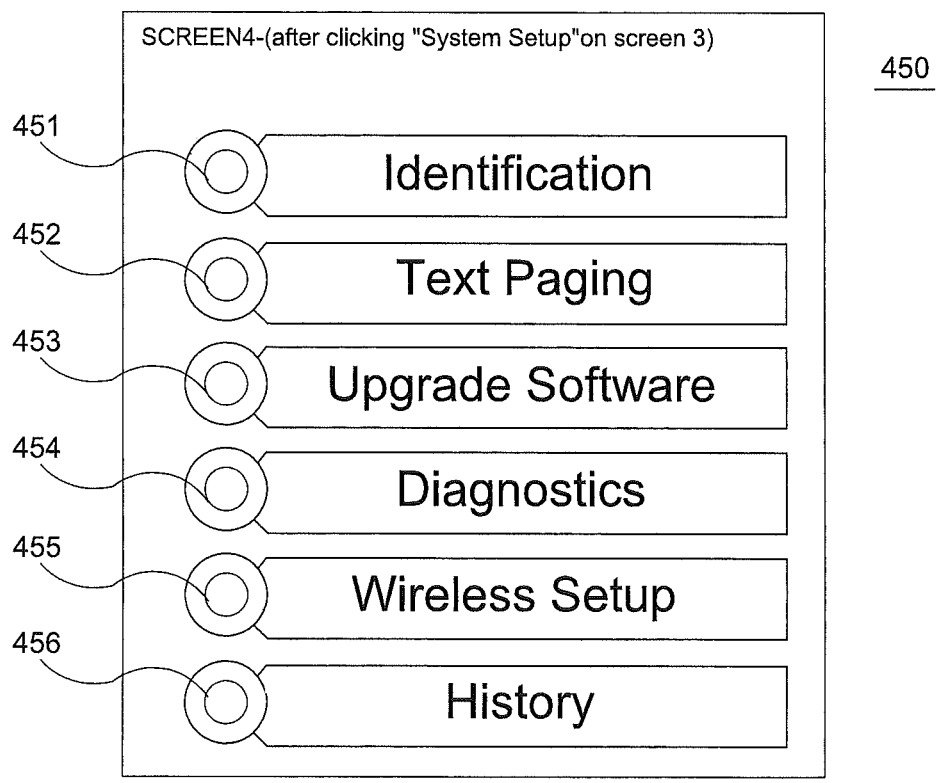
FIGS. 4(b) and 4(c) illustrate exemplary screen displays for commanding a medical device according to the method of FIG. 4(a)

FIG. 4(*a*) presents a flow diagram illustrating an exemplary method 400 in accordance with the invention for issuing a command to a medical device 10 via the system 100 according to FIG. 1. The method 400 begins at step 402 with an authorized user adjusts an operating parameter, such as a clinician (also referred to as a "authorized clinician" or "user" herein) logging into the outbound web server 43 using a first remote monitoring device 62 and navigating to the device screen display 340 of FIG. 3(*d*) (for example, as described above with reference to FIGS. 3(a)-3(d)). At step 404, the clinician proceeds to select the "Enable Full Control" button 347F of FIG. 3(d) to initiate an operational command directed to the medical device 10, and is preferably provided with a request for authentication pertaining in particular to the patient associated with the medical device 10. At step 406, patient authentication information provided by the clinician is forwarded by the outbound web server 43 to a patient care database node 60 according to a patient care database node address stored by the metadata and applications database 46 in association with the clinician, and the clinician is authenticated for the patient by the outbound web server 43 upon receipt of an authentication confirmed message from the patient care database node 60.

Upon receipt of the patient authentication, a control request is forwarded by the outbound web server 43 at step 408 to the secure device web server 42 to be logged in the information record of the device control database 44 that is associated with the medical device 10 (and optionally, with an anonymous ID for the patient). At step 410, the secure device web server forwards the control request, such as an encrypted control request, to the device integration server 41, which transmits an associated device control command over the secure WWAN 52 for receipt by an associated wireless relay module 30 at step 412. The wireless relay module 30 wirelessly communicates the command to the medical device 10 via an associated device interface 15, and awaits a reply confirming execution of the command transmitted by the device interface 15.

At step 414, the device integration server 41 receives an update message from the wireless relay module 30 via the secure WWAN 52 which confirms that the command was executed by the medical device 10. At step 416, the device integration server 41 forwards the update message to the secure device web server 42 to be logged in the information record of the device control database 44 that is associated with the medical device 10. Optionally, and preferably, the secure device web server 42 forwards information pertaining to the update message to the outbound web server 43, and the outbound web server 43 prepares an updated display screen that is securely transmitted to the remote monitoring device 62 to indicate that the command has been executed.

Alternatively, at step 404, the authenticated clinician may select the "System Setup" control icon button 347E to perform a command other than an operational command directed to the medical device 10. FIG. 4(b) illustrates a display screen 450 that is presented to the clinician upon selecting the control icon button 347E. The display screen 450 includes a number of icon buttons that may be selected by the clinician (for example, as the result of a mouse-over or mouse-click initiated by the clinician) to select a specific setup command. For example, icon button 451 may be selected to initiate a command for providing identification information of the medical device 10. Icon button 452 may be selected to provide text paging in response to an alert condition, as is further described herein. Icon button 453 may be selected to initiate a software or firmware download for updating the medical device 10.

Icon button 454 may be selected to initiate a diagnostic test of the medical device 10. FIG. 4(c) illustrates an exemplary display screen 460 that may be displayed to the clinician upon selection of the icon button 454. Via the display screen 460 of FIG. 4(C), the clinician may select one or more of (including a progression of) a series of diagnostic tests 461 directed to components of the medical device (for example, including power components, memory components, alarm components and the like). Alternatively and/or in addition, the clinician may select one or more of a series of performance statistics 462 to be gathered and displayed (for example, including various device error statistics such as feed error, rotor error and flush error rates for a food pump). In addition, perhaps most usefully before issuing a software and/or firmware download command, the clinician may select a version number test 463 to obtain version identifying information for the software and/or firmware (preferably including, for example, a software and/or firmware download history). Optionally, processes for performing the diagnostic tests 461, preparing the performance statistics 462 and identifying the software and/or firmware version number 463 may run automatically without specifically being selected by the clinician, with a complete reporting of all results on the display screen.

In a similar manner to that performed by the method of FIG. 4(a), it is possible to issue a bandwidth priority command or instruction to a relay module, such as relay module 30 of FIG. 1, for the relay module to grant priority for relaying information received from a particular medical device relative to other medical devices that may send or receive communications via this relay module. For example, it would be advantageous to provide greater bandwidth priority to a critical care device such as a ventilator supporting the breathing function of a patient relative to a weight scale or thermometer. It is also possible to a number of bandwidth priority levels assignable to respective medical devices based upon, for example, the critical nature of the data or function provided by such devices.

Referring again to FIG. 4(b), icon button 455 may be selected to enable the clinician to specify data transfer rates, priorities and other parameters relating to the wireless transceiver of the interface device associated with the medical device. Icon button 456 may be selected to provide the clinician with the an alarm history, event history and other information as has been logged for example for the medical device in the device control database 44 of FIG. 1.

It should be readily understood that the method 400 for remotely issuing a command to a medical device 10 was described with respect to a user of a first remote monitoring device 62 and not a user of the second remote monitoring 70, 75 because as described for example throughout this application, it is assumed that the user of the first remote monitoring device 62 is a clinician, technician or other highly-skilled healthcare professionals, while the user of the second remote monitoring device 70, 75 may be a patient relative or caregiver of lesser skill. Nevertheless, the method 400 is likewise useable to enable a user of the second monitoring device 70, 75 to also control particular settings of the medical device 10.

Figure 5A:
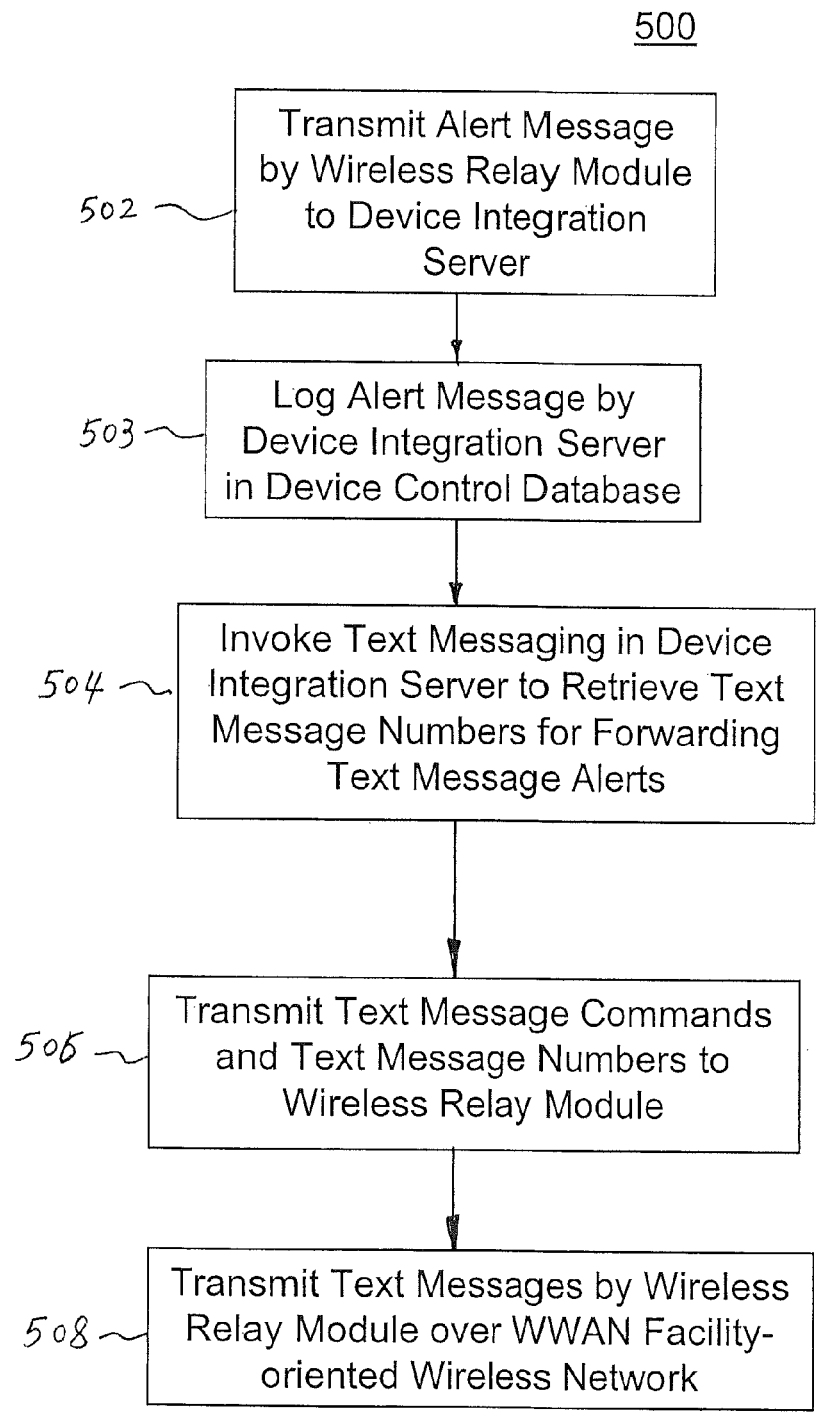
FIG. 5(a) presents a flow diagram illustrating an exemplary method for recognizing and reporting an alert condition according to medical data logged via the remote monitoring system according to FIG. 1.

FIG. 5(a) presents a flow diagram illustrating one exemplary method 500 in accordance with the invention for recognizing and reporting an alert condition according to medical device data (including the status of the facility-oriented network 17) logged via the system 100 according to FIG. 1. The method 500 begins at step 502 with the transmission of an alert message by a wireless relay module 30 over the secure WAN 52 to the device integration server 41. In this case, the wireless relay module 30 is configured to analyze (such as by detecting flag or status information or comparing message data to information stored in an associated database) a message type of a message transmitted by an associated medical device 10 to determine that the message is an alert message, and to transmit the message to the device integration server 41 upon determining that the message is an alert message (for example, as a priority message). Alternatively, the wireless relay module 30 may simply queue all messages for transmission to the device integration server 41 in order upon receipt, and rely upon the device integration server 41 to analyze an associated message type to determine that a message is an alert message.

Upon determining that the transmitted message is an alert message, the device integration server 41 proceed, at step 503, to log the message in the device control database 44, and at step 504, invokes a text messaging application that retrieves text messaging numbers associated with identifying information of the medical device 10 and/or anonymous patient identifying information. The determination of whether the transmitted message is an alert message may be carried out by, for example, detecting an alert flag or trigger identifier in the message or scanning the message for other information indicative of an alert condition. The text messaging application may preferably retrieve the text messaging numbers by querying the metadata and applications database 46 to identify the address of an associated patient care database node 60, and either making a direct request or instructing the outbound web server 43 to request the text messaging numbers from the associated patient care database node 60.

At step 506, the device integration server 41 sends one or more messages including the retrieved text messaging numbers and text message information according to the alert message to one or more wireless relay modules 30 over the secure WWAN 52. At step 508, the one or more wireless relay modules 30 transmit the text message information addressed to the text messaging numbers over one or more of the secure WWAN 52 and/or the facility-oriented wireless network 17 to complete the method 500.

FIG. 5(*b*) illustrates a "Text Paging" 452 screen display 550 that may be invoked, for example, by using the method 400 of FIG. 4(*a*) for issuing a command to a medical device 10. Specifically, and with particular reference to FIGS. 3(*d*) and 4(*b*), the text paging screen 550 is displayed at the first remote monitoring device 62 of an authenticated clinician upon the clinician's selection of the "System Setup" icon button 347*e* of the screen display 340, and thereafter upon the clinician's selection go the "Text Paging" icon button of the screen display 450. Likewise, it is possible for the paging screen 550 of FIG. 5(*b*) to be displayed on a second remote monitoring device 70, 75 for completion by an authorized user, such as a patient relative or other caregiver. As illustrated in FIG. 5(*b*), the "Text Paging" screen display 550 include a listing of one or more names 551 of individuals responsible for responding to alert messages of at least two types: "Error Messages" 553, which may for example indicate a malfunction of the medical device 10, and/or "Info Messages" 554, which may for example indicate a significant patient health condition (for example, a patient respiration rate below a preset minimum rate specified for a ventilator device 321 of FIG. 3(*b*)).

The information retrieved by the outbound web server 43 to prepare this display is preferable retrieved from the patient care database node 60, by providing on one or more of identifying information for the medical device 10 and/or anonymous patient identifying information stored in the device control database 44. Upon recognizing an alert message for the medical device 10, the information provided on the "Text Paging" screen display may be retrieved by the device integration server 41 by querying the metadata and applications server 46 to retrieve address information for the patient care database node 60, and forwarding a text paging information request to the patient care database node 60 based upon one or more of identifying information for the medical device 10 and/or anonymous patient identifying information stored in the device control database 44. The recognition of whether the received message from the medical device 10 is an alert message may be carried out by, for example, detecting an alert flag or trigger identifier in the message or scanning the message for other information indicative of an alert condition.

It should be readily understood that the use of communicating alert messages using text messaging in FIGS. 5(*a*) and 5(*b*) is for ease of illustration purposes only and that such alerts may be communicated in other ways in accordance with the present invention including email, audio messages via telephone calls, as well as any other wired and/or wireless text, audio, or multimedia based communication services receivable by, for example, by a smart phone or computer tablet software application or "App."

Figure 6:
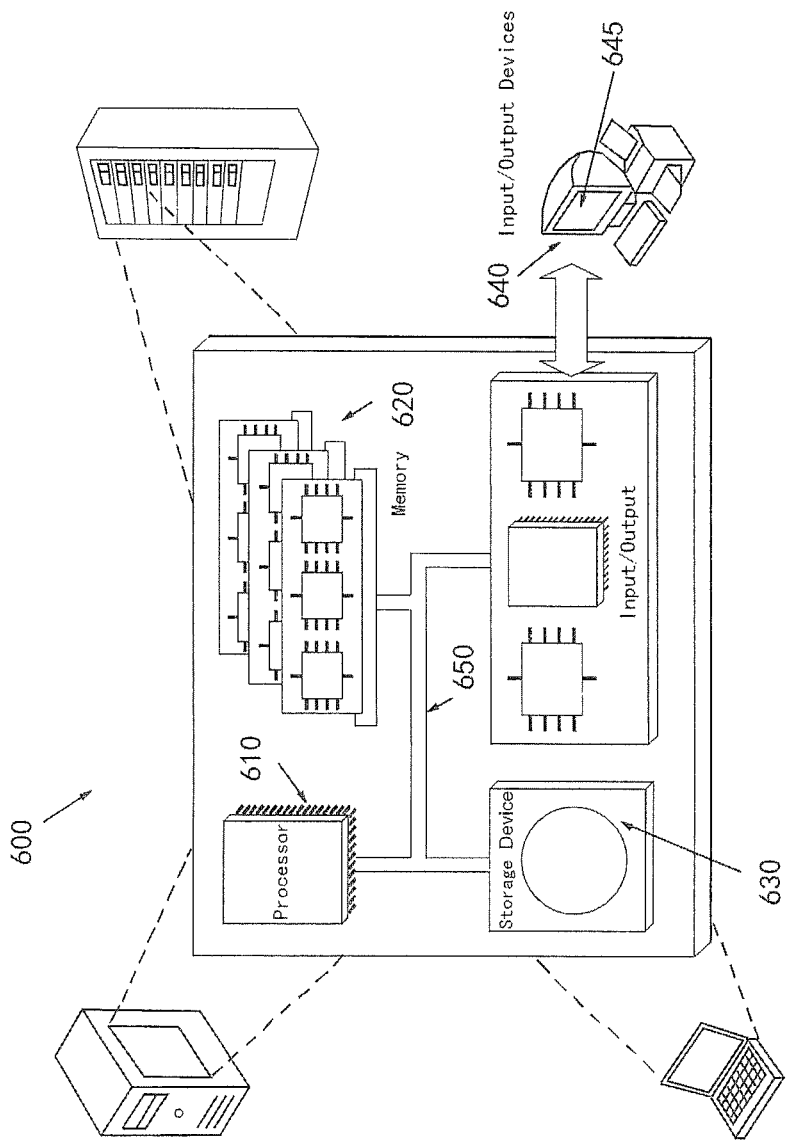
FIG. 6 presents a block diagram of an exemplary computer or server device suitable for use in the remote monitoring system according to FIG. 1.

FIG. 6 shows an illustrative computer system 600 suitable for implementing server and computer components of the present invention (for example, including device integration server 41, secure device web server 42, outbound web server 43, and secure patient web server 64). The computer system 600 as described herein may comprise, for example, a personal computer running the WINDOWS operating system, or a server computer running, WINDOWS Server, LINUX or another UNIX-based operating system. Alternatively, the computer system 600 described herein may comprise a mobile device, tablet devices or computers, or information appliance running, for example, an operating system in the group including Symbian, Android, Apple iOS, Blackberry, Microsoft Windows Phone, Linux, Palm/HP WebOS, BADA, MAEMO and MEEGO. The above-described methods carried out by the server and computer components of the present invention may be implemented on the computer system 600 as stored program control instructions directed to control application software.

Computer system 600 includes processor 610, memory 620, storage device 630 and input/output devices 640. One of the input/output devices 640 may preferably include a display 645. Some or all of the components 610, 620, 630 and 640 may be interconnected by a system bus 650. Processor 610 may be single or multi-threaded, and may have one or more cores. Processor 610 executes instructions which in the disclosed embodiments of the present invention are the steps described, for example, in one or more of FIG. 2, 3(*a*), 4(*a*) or 5(*a*). These instructions may be stored in one or more of memory 620 or in storage device 630. Information may be received and output using one or input/output devices 640. Memory 620 may store information and may comprise a computer-readable medium, such as volatile or non-volatile memory. Storage device 630 may provide storage for system 600 including for the example, the previously described database, and may be a computer-readable medium. In various aspects, storage device 630 may be one or more of a flash memory device, a floppy disk drive, a hard disk device, and optical disk device, and/or a tape device.

Input devices 640 may provide input/output operations for system 600. Input/output devices 640 may include one or more of a keyboard, a pointing device, and/or microphone. Input/output devices 640 may further include a display unit for displaying graphical user interfaces, a speaker and a printer and any of a number of other serial devices (for example, configured as Universal Serial Bus (USB)-based devices It should of course, be understood that while the present invention has been described with respect to disclosed embodiments, numerous variations are possible without departing from the spirit and scope of the present invention as defined in the claims.

Moreover, it is intended that the scope of the present invention include all other foreseeable equivalents to the elements and structures as described herein and with reference to the drawing figures. Accordingly, the invention is to be limited only by the scope of the claims and their equivalents.

We claim:

1. A system for enabling remote monitoring of a plurality of medical devices, the system comprising:
two or more wireless relay modules forming a wireless relay network, each of the two or more wireless relay modules having a first transceiver configured to receive signals from and transmit signals to at least two of the plurality of medical devices in communication with the wireless relay network, and a second transceiver configured to be in communication with an internet-accessible wireless network, each medical device configured to communicate with one or more of the wireless relay modules;
a database configured to have stored therein a set of safe operating parameters for the plurality of medical devices, a set of unsafe operating parameters for the plurality of medical devices, and a set of conditions for the plurality of medical devices for determining whether a command sent to one of the medical devices is an unsafe command;
a device integration server in communication with the two or more wireless relay modules, wherein said two or more wireless relay modules are configured to transmit data packets containing information provided by any of the plurality of medical devices, wherein each of said data packets includes medical device data and at least a medical device identifier or a patient identifier, and wherein said device integration server is configured to monitor commands sent to the medical devices to prevent unsafe medical device usage by accessing the database to evaluate the safe and unsafe operating parameters for a medical device, and the conditions for determining whether a command sent to at least one of the plurality of medical devices is an unsafe command;
a data manager system coupled to said device integration server, said data manager system comprising at least a device control database; and
a web server configured for providing web pages for receiving at least the medical device data, formatting the medical device data as first medical device data based upon a type of user authenticated on a first remote monitoring device, and transmitting the first medical device data to the first remote monitoring device via a secure internet connection for displaying the first medical device data at the first remote monitoring device and formatting the medical device data as second medical device data based upon a second type of user authenticated on a second remote monitoring device, and transmitting the second medical device data to the second remote monitoring device for displaying the second medical device data at the second remote monitoring device.

2. The system of claim 1 wherein the web server is configured for verifying one or more of the patient identifier or the medical device identifier before transmitting the first medical device data to the first remote monitoring device.

3. The system of claim 1 wherein said web server is configured to transmit the second medical device data to the second remote monitoring device by at least a wireless data link.

4. The system of claim 3 wherein said wireless data link is over a wireless mobile data network.

5. The system of claim 1 wherein the second remote monitoring device is a portable communications device of at least one of a mobile phone, tablet computer and portable computer.

6. The system of claim 1 wherein said web server is configured to transmit to at least one of the first and the second remote monitoring devices, status information concerning the wireless relay network.

7. The system of claim 1 wherein the second remote monitoring device is located in a same facility as a patient for use by a local caregiver.

8. The system of claim 1 wherein the first medical device data displayed by the first remote monitoring device and the second medical device data displayed by the second remote monitoring device are different.

9. The system of claim 8 wherein the first medical device data displayed by the first remote monitoring device includes data for use by a clinician and the second medical device data displayed on the second remote monitoring device includes data for use by a caregiver.

10. The system of claim 1 wherein, if a first authenticated user is a clinician, the first medical device data is formatted to include controls to allow the clinician to adjust settings of the at least one medical device.

11. The system of claim 10 wherein, if the first authenticated user is not a clinician, the first medical device data is formatted to exclude controls to allow the authenticated user to adjust the settings of the at least one medical device.

12. The system of claim 1 wherein the second remote monitoring device includes a function for sending messages to and/or paging a clinician.

13. The system of claim 1 wherein the device integration server is configured to discard a command associated with unsafe medical device usage prior to the command reaching the medical device and/or provide a notification of an unsafe condition in response to monitoring the commands.

14. The system of claim 1 wherein the device control database includes a list of medical devices that are presently active.

15. The system of claim 14 wherein the plurality of medical devices are programmed to provide data to the integration server at predetermined intervals.

16. A system for enabling remote monitoring of a plurality of medical devices, the system comprising:
two or more wireless relay modules forming a wireless relay network, each of the two or more wireless relay modules having a first transceiver configured to receive signals from and transmit signals to at least two of the plurality of medical devices in communication with the wireless relay network, and a second transceiver configured to be in communication with an internet-accessible wireless network, each medical device configured to communicate with one or more of the wireless relay modules;
a database configured to have stored therein a set of safe operating parameters for the plurality of medical devices, a set of unsafe operating parameters for the plurality of medical devices, and a set of conditions for the plurality of medical devices for determining whether a command sent to one of the medical devices is an unsafe command;
a device integration server in communication with the two or more wireless relay devices, wherein said two or more wireless relay devices are configured to transmit data packets containing information provided by the plurality of medical devices including medical device data and at least one of medical device identifier and a patient identifier, and wherein said device integration server is configured to monitor commands sent to the plurality of medical devices to prevent unsafe medical device usage by accessing the database to evaluate the safe and unsafe operating parameters for a medical device, and the conditions for determining whether a command sent to at least one of the plurality of medical devices is an unsafe command;

a data manager system coupled to said device integration server, said data manager system comprising: a device control database;

a web server configured for:
providing web pages for receiving at least the medical device data;
formatting the medical device data as first medical device data based upon a type of user authenticated on a first remote monitoring device;
formatting the medical device data as second medical device data based upon a type of user authenticated on a second remote monitoring device; and,
subject to verification of the patient identifier and/or the medical device identifier, transmitting the medical device data to first and second remote monitoring devices via a secure internet connection for displaying the medical device data at the first and second remote monitoring devices; and a network status server configured for transmitting to at least one of the first or second remote monitoring devices, status information concerning the wireless relay network associated with the at least two wireless relay devices.

17. The system of claim 16 wherein said network status server is located at a different geographic location than the web server.

18. A system for enabling remote monitoring a plurality of medical devices, the system comprising:

two or more wireless relay modules forming a wireless relay network, each of the two or more wireless relay modules having a first transceiver configured to receive signals from and transmit signals to at least two of the plurality of medical devices in communication with the wireless relay network, and a second transceiver configured to be in communication with an internet-accessible wireless network, each medical device configured to communicate with one or more of the wireless relay modules;

a database configured to have stored therein a set of safe operating parameters for the plurality of medical devices, a set of unsafe operating parameters for the plurality of medical devices, and a set of conditions for the plurality of medical devices for determining whether a command sent to one of the medical devices is an unsafe command;

a device integration server in communication with the two or more wireless relay modules, wherein said two or more wireless relay devices are configured to transmit data packets containing information provided by the plurality of medical devices, wherein each of said data packets includes medical device data and at least a medical device identifier or a patient identifier, and wherein said device integration server is configured to monitor commands sent to the plurality of medical devices to prevent unsafe medical device usage by accessing the database to evaluate the safe and unsafe operating parameters for a medical device and conditions for determining whether a command sent to at least one of the plurality of medical devices is an unsafe command;

a data manager system coupled to said device integration server, said data manager system comprising at least a device control database, and a web server configured for providing web pages for receiving at least the medical device data and transmitting the medical device data to a first remote monitoring device via a secure internet connection for displaying the medical device data at the first remote monitoring device; and transmitting at least a portion of the medical device data to a second remote monitoring device for displaying the portion of the medical device data at the second remote monitoring device.

19. The system of claim 18 wherein the web server is configured for formatting the medical device data as first medical device data based upon a type of user authenticated on a first remote monitoring device and transmitting the first medical device data to the first remote monitoring device for displaying the first medical device data at the first remote monitoring device.

20. The system of claim 19 wherein the web server is configured for formatting the medical device data as second medical device data based upon a second type of user authenticated on a second remote monitoring device, and transmitting the second medical device data to the second remote monitoring device for displaying the second medical device data at the second remote monitoring device.

21. The system of claim 18 wherein the device integration server is further configured to determine whether a particular command of the commands sent to the at least one of the plurality of medical devices is an unsafe command based on the safe operating parameters, the unsafe operating parameters, and/or the conditions.

22. The system of claim 21 wherein the device integration server is further configured, upon determination that the particular command is an unsafe command, to discard the unsafe command.

23. The system of claim 18 wherein the device integration is further configured, upon determination that the particular command is an unsafe command, to provide a warning message.

24. The system of claim 18 wherein the device integration server is further configured, upon determination that the particular command is an unsafe command, to program the medical device with information that deviates from the particular command.

* * * * *